(12) United States Patent
Takahashi

(10) Patent No.: US 7,563,259 B2
(45) Date of Patent: Jul. 21, 2009

(54) OPERATION SYSTEM

(75) Inventor: Hiroyuki Takahashi, Akishima (JP)

(73) Assignee: Olympus Corporation (JP)

( * ) Notice: Subject to any disclaimer, the term of this patent is extended or adjusted under 35 U.S.C. 154(b) by 102 days.

(21) Appl. No.: 10/958,868

(22) Filed: Oct. 5, 2004

(65) Prior Publication Data

US 2005/0080403 A1    Apr. 14, 2005

Related U.S. Application Data

(63) Continuation of application No. PCT/JP03/12654, filed on Oct. 2, 2003.

(51) Int. Cl.
*A61B 17/00* (2006.01)
*A61B 18/04* (2006.01)
*A61B 18/18* (2006.01)

(52) U.S. Cl. .............. 606/1; 606/27; 606/34; 128/903

(58) Field of Classification Search .......... 606/1, 606/27, 34; 128/903
See application file for complete search history.

(56) References Cited

U.S. PATENT DOCUMENTS

| | | | | |
|---|---|---|---|---|
| 5,417,687 A | * | 5/1995 | Nardella et al. | 606/32 |
| 5,437,662 A | * | 8/1995 | Nardella | 606/40 |
| 6,074,388 A | | 6/2000 | Tockweiler et al. | |
| 6,245,065 B1 | * | 6/2001 | Panescu et al. | 606/40 |
| 6,768,425 B2 | * | 7/2004 | Flaherty et al. | 340/870.07 |
| 2003/0171740 A1 | * | 9/2003 | Stiller et al. | 606/1 |

FOREIGN PATENT DOCUMENTS

| | | |
|---|---|---|
| JP | 11-318935 | 11/1999 |
| JP | 11-332883 | 12/1999 |
| JP | 2000-139945 | 5/2000 |
| JP | 2000-287989 | 10/2000 |
| JP | 2001-283368 | 10/2001 |
| JP | 2001-313983 | 11/2001 |
| JP | 2002-58678 A | 2/2002 |
| WO | WO02/49509 * | 6/2002 |
| WO | WO 02/49509 A2 | 6/2002 |

* cited by examiner

*Primary Examiner*—Lee S Cohen
(74) *Attorney, Agent, or Firm*—Scully, Scott, Murphy & Presser, P.C.

(57) ABSTRACT

In an operation system according to the present invention, a radio foot switch is turned on and a pedal is pressed. Further, a medical device as a control target is turned on and a signal indicating the press operation of the pedal is transmitted together with an ID code. The medical device as the control target receives the signal and stores the ID code, thus to enter an identification state of a remote control device. The medical device returns the ID code and thus the radio foot switch stores the ID code so that the radio foot switch identifies, based on the returned ID code, the medical device which transmits the ID code as the control target. Then, upon pressing the pedal, an operating signal is transmitted to the ID code of the medical device as the control target and thus the remote control operation is possible without fail between the radio foot switch and the medical device as the control target which are not specified.

9 Claims, 16 Drawing Sheets

OPERATION SYSTEM

CROSS REFERENCE TO RELATED APPLICATION

This application is a continuation application of PCT/JP03/12654 filed on Oct. 2, 2003 the disclosure of which is incorporated herein by its reference.

TECHNICAL FIELD

The present invention relates to an operation system which performs the operation by using a medical device.

BACKGROUND ART

As one conventional art, Japanese Unexamined Patent Application Publication No. 2000-287989 discloses an ultrasonic operation apparatus which uses a method for controlling an ultrasonic output by switching on/off a foot switch connected by wiring.

Further, Japanese Unexamined Patent Application Publication No. 11-318935 discloses a wiring foot switch integrally comprising a plurality of switches for controlling a plurality of medical devices, which uses a method for controlling the medical devices by detecting the user's foot position, by displaying the medical device corresponding to an effective switch on a display portion, and by switching on/off the foot switch.

Furthermore, Japanese Unexamined Patent Application Publication No. 11-332883 discloses one wiring foot switch for controlling a plurality of medical devices, which uses a method for switching the medical device controlled by the foot switch by user's voice and for displaying, on a display portion, information on the medical device selected by the voice.

The foot switch is connected to the medical devices by wiring. Therefore, when a plurality of medical devise are arranged to an operation room, the number of cords corresponding to the number of medical devices are wired on the floor and the cords become a problem because the user's foot is caught by the cord and the user must step over the cord.

In order to solve the above-mentioned problems, recently, a radio foot switch without any cord has been developed. However, the radio propagation has a specific problem that electric waves are propagated over the wide range and therefore only a specific medical device cannot be controlled.

According to a method for controlling only the specific medical device by providing a specific ID for the medical device and the foot switch, the foot switch in this case is dedicated for the corresponding medical device and, upon using a plurality of medical devices, a plurality of foot switches are still provided and the problem that the cords occupy the floor of the operation room is not solved.

Further, when one of the corresponding medical device and the corresponding foot switch is damaged, there is a problem of the maintenance that the two devices must be repaired because of the specific IDS of the two devices.

In addition, when the foot switch is not found, the medical device is not controlled with the same-functional foot switch having another ID. Thus, the operation is interrupted.

It is one object of the present invention to provide an operation system which solves the problem that it is possible to use only when a medical device and a remote control device, such as a foot switch, have specific ID information in common.

Further, it is another object of the present invention to provide an operation system with preferable operability, which can remotely control an arbitrary medical device without limiting a remote control device such as a foot switch to a specific medical device.

DISCLOSURE OF INVENTION

In an operation system according to the present invention, a radio foot switch is turned on, a pedal is pressed, and a medical device as a control target is turned on. Then, a signal outputted by pressing the pedal is transmitted together with an ID code. The medical device as the control target receives the transmitted signal, and stores the ID code so as to identify a remote control device. Further, the medical device returns the ID code and, thus, the radio foot switch stores the ID code so as to identify, as the medical device as the control target, the medical device which transmits the ID code. After that, upon pressing the pedal, an operating signal is transmitted to the ID code of the medical device as the control target and thus the remote control operation is possible without fail when the radio foot switch is not dedicated to the medical device as the control target.

BEST MODE FOR CARRYING OUT THE INVENTION

Hereinbelow, embodiments of the present invention will be described with reference to the drawings.

First Embodiment

An electric operation system according to the first embodiment of the present invention comprises one radio foot switch and a plurality of medical devices. The operation for pressing the radio foot switch corresponds to the operation for turning on/off one medical device.

Figure 1:
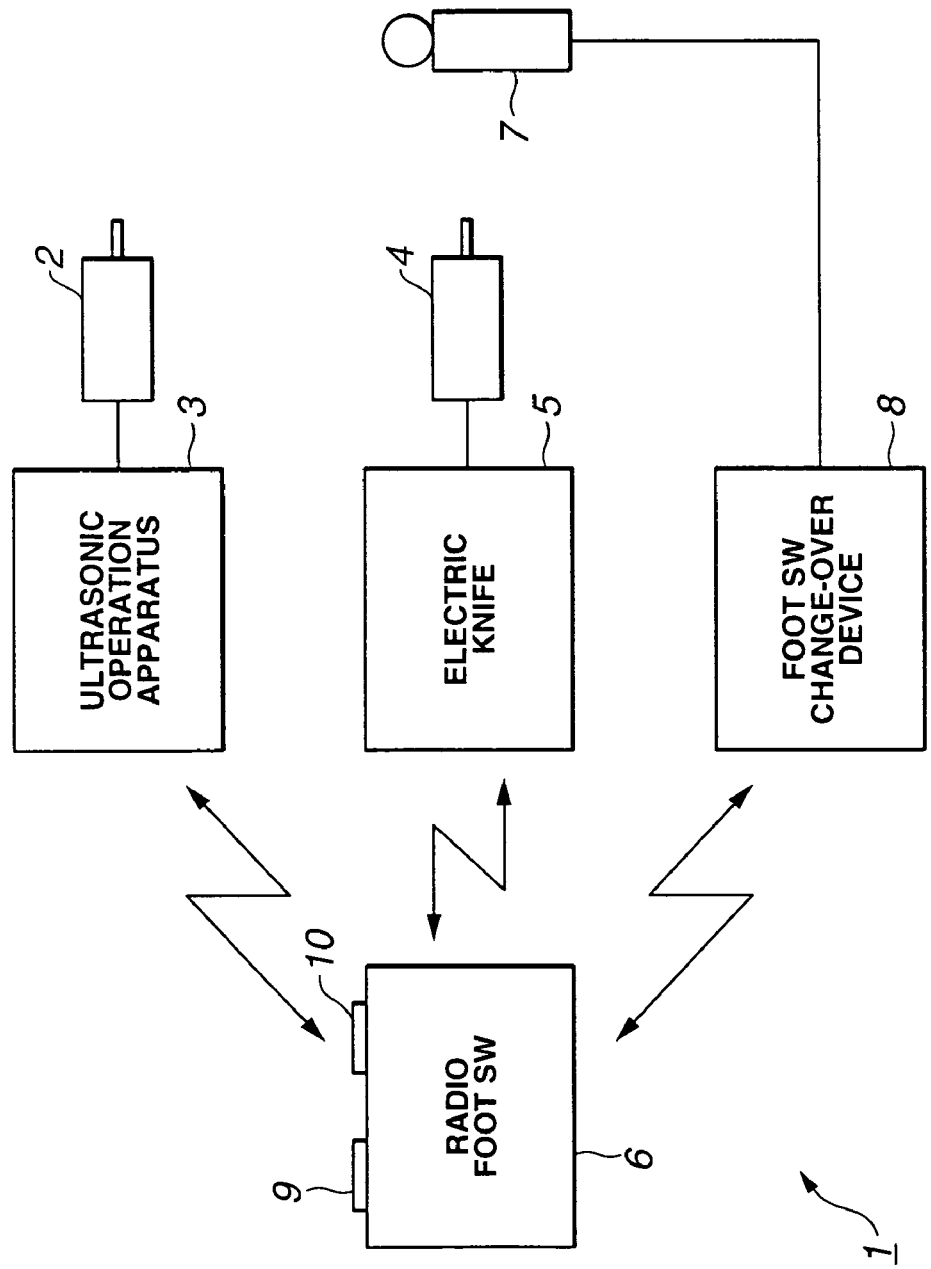
FIG. 1 is a diagram showing the entire structure of an electric operation system according to the first embodiment of the present invention.
Figure 2:
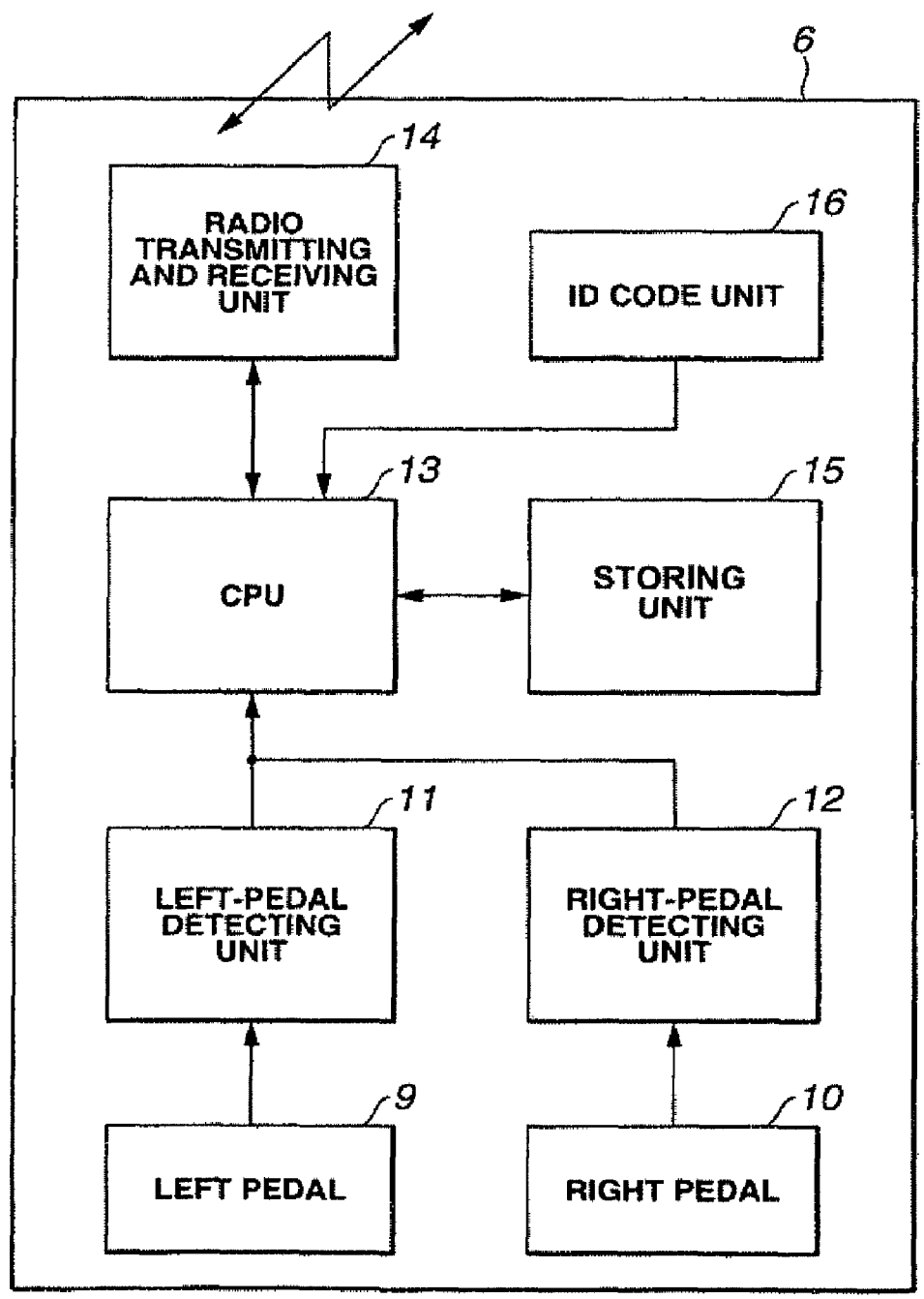
FIG. 2 is a block diagram showing the schematic structure of a radio foot switch according to the first embodiment.
Figure 3:
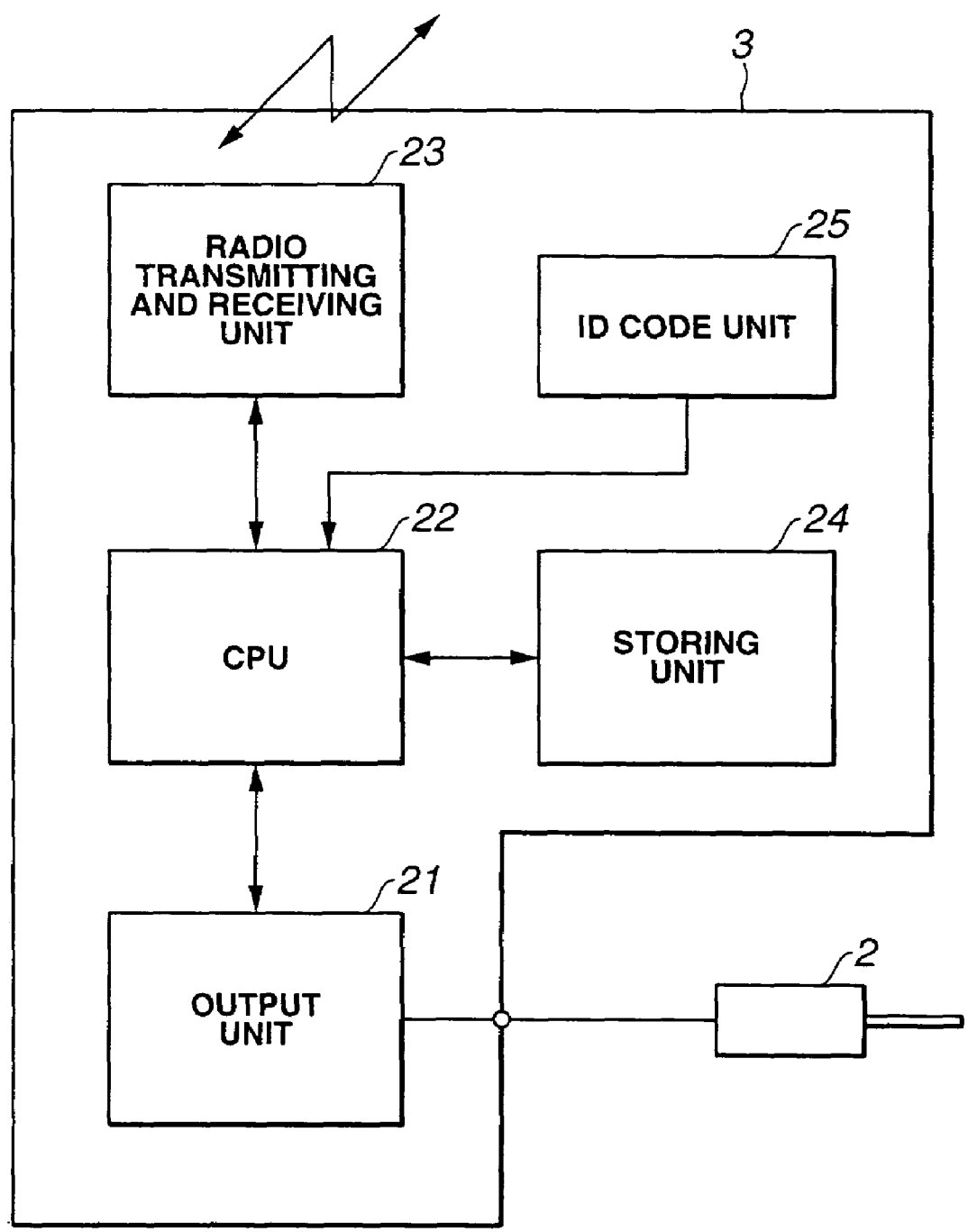
FIG. 3 is a block diagram showing the schematic structure of an ultrasonic operation apparatus according to the first embodiment.
Figure 4:
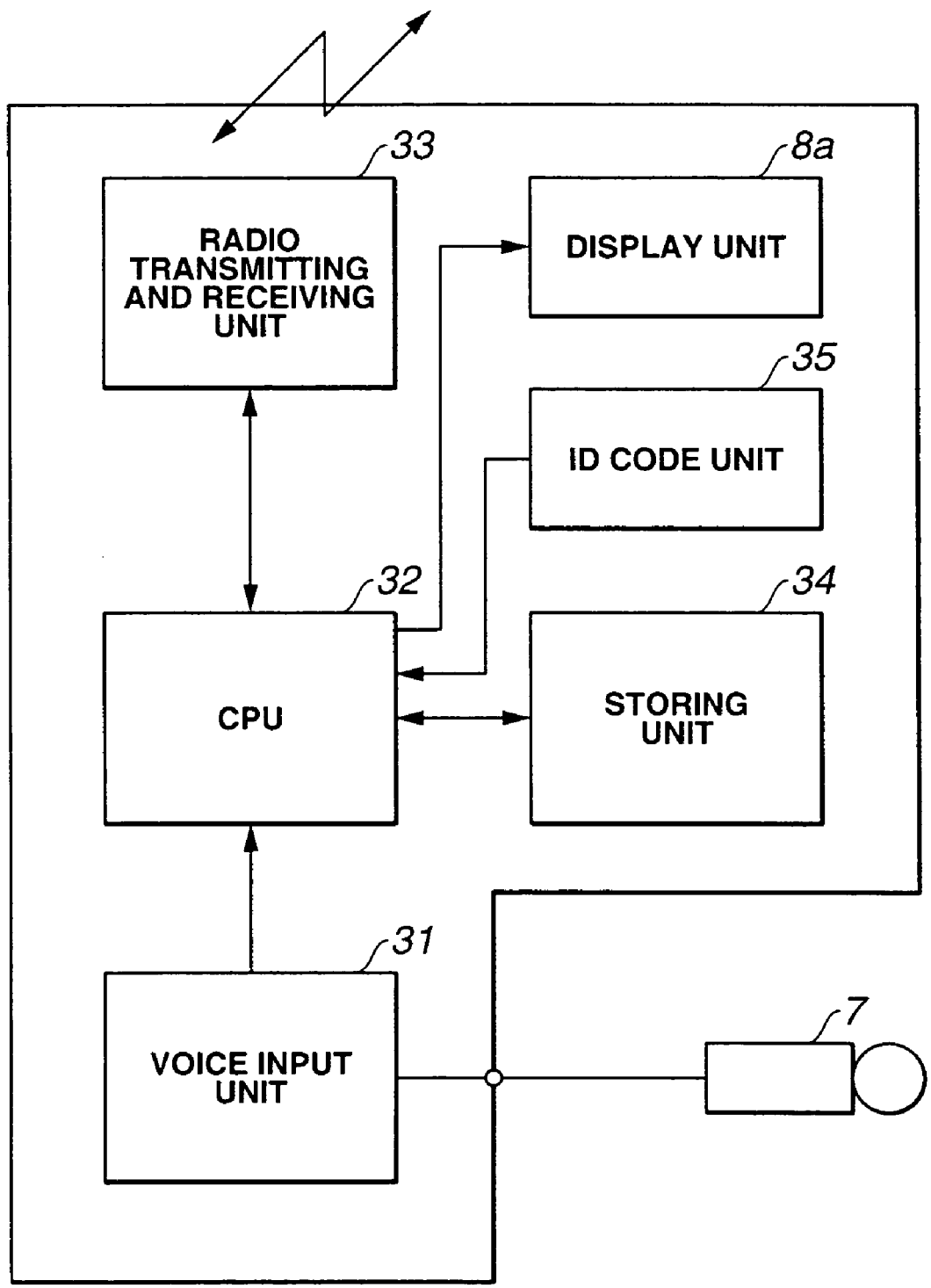
FIG. 4 is a block diagram showing the schematic structure of a foot switch change-over device according to the first embodiment.
Figure 5:
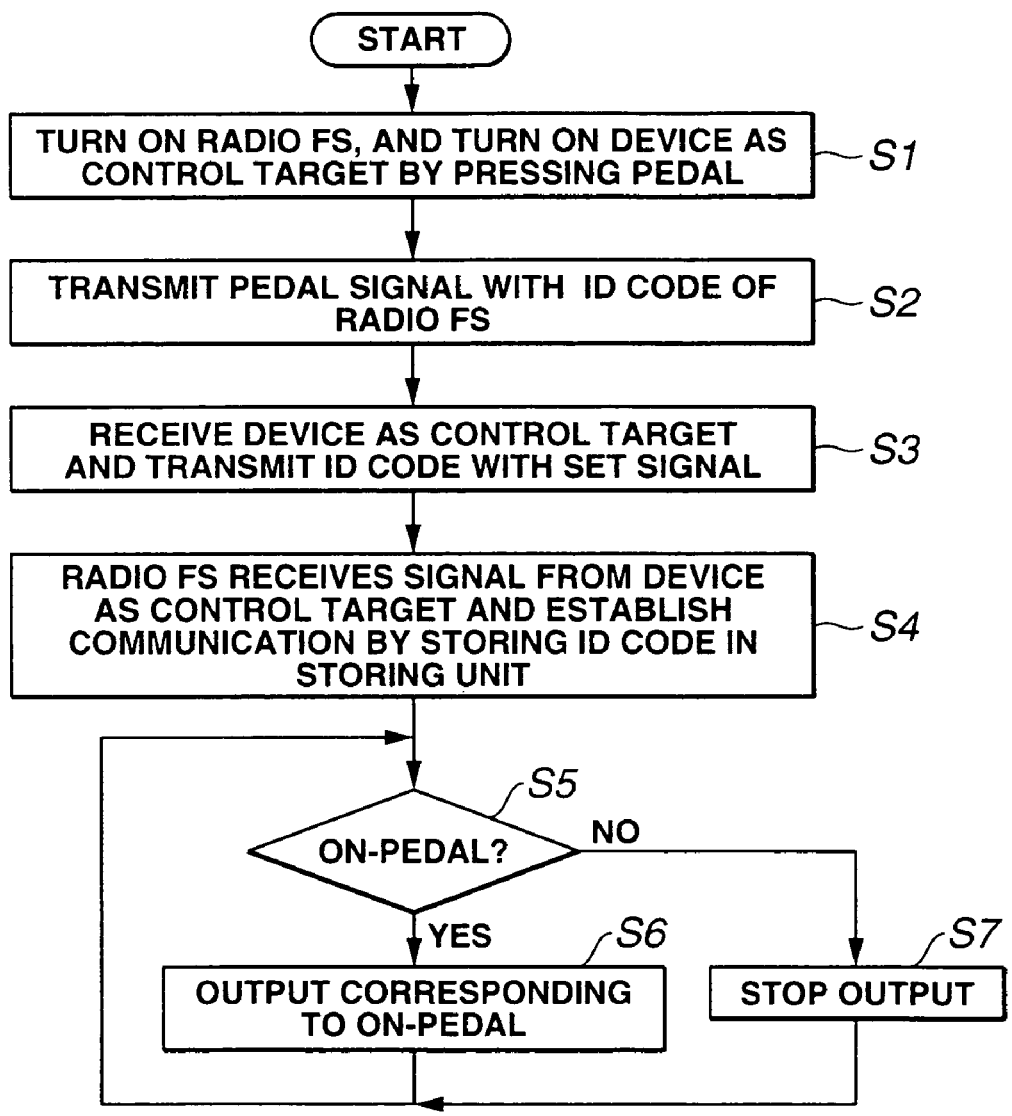
FIG. 5 is a flowchart showing the control operation according to the first embodiment.

FIGS. 1 to 5 relate to the first embodiment of the present invention. FIG. 1 is a diagram showing the entire structure of the electric operation system according to the first embodiment of the present invention. FIG. 2 is a block diagram showing the schematic structure of a radio foot switch shown in FIG. 1. FIG. 3 is a block diagram showing the schematic structure of an ultrasonic operation apparatus shown in FIG. 1. FIG. 4 is a block diagram showing the schematic structure of a foot switch change-over device. FIG. 5 is a flowchart showing the control operation according to the first embodiment.

Referring to FIG. 1, the electric operation system 1 according to the first embodiment comprises: a plurality of medical devices such as, an ultrasonic operation apparatus 3 having a plurality of connected medical devices, e.g., ultrasonic treatment tools 2 for ultrasonic operation; an electric knife (device) 5 connected to an electric knife treatment tool 4 for applying high-frequency current for the operation; a radio foot switch 6, as a remote control device, which can remotely control, by radio waves, the operation of the ultrasonic operation apparatus 3 and the electric knife 5; and a foot switch change-over device 8 which switches the radio foot switch 6 by voice from a microphone 7. According to the first embodiment, the microphone 7 for the foot switch change-over device 8 is not absolutely necessary and the microphone 7 will be described according to the second embodiment.

According to the first embodiment, the radio foot switch 6 comprises, e.g., a left pedal 9 and a right pedal 10. The left pedal 9 and the right pedal 10 are pressed, thereby controlling corresponding operations, e.g., the on/off operation of the output from the ultrasonic operation apparatus 3 or the electric knife 5.

FIG. 2 shows the structure of a main portion of the radio foot switch 6.

The radio foot switch 6 comprises: a left-pedal detecting unit 11 and a right-pedal detecting unit 12 which detect whether the left pedal 9 or right pedal 10 is pressed for the on-operation; a CPU 13 which receives a detecting signal from the left-pedal detecting unit 11 or right-pedal detecting unit 12 and performs the corresponding control operation; a radio transmitting and receiving unit 14 which is connected to the CPU 13, and transmits radio information and receives the radio information; a storing unit 15 which is connected to the CPU 13, stores the program of the CPU 13 that controls the operation of the radio foot switch 6, and stores information including an ID code as identification information of the medical device whose transmission is controlled; and an ID code unit 16 which stores the ID code as the identification information specified to the radio foot switch 6.

As will be described later, the storing unit 15 stores the ID code as the identification information of the medical device which can be transmission-controlled. After that, the left pedal 9 or right pedal 10 is pressed, and the CPU 13 controls the radio transmitting and receiving unit 14 and the like so that the signal corresponding to the function of the left pedal 9 or right pedal 10 is transmitted to the corresponding medical device together with the ID code (for selective designation) of the corresponding medical device.

Further, the radio-transmitted information is received and the medical device having the ID code matching the ID code in the information performs the operation corresponding to the function of the pressed left pedal 9 or right pedal 10.

As mentioned above, the medical device that is transmission-controlled is set, then, the CPU 13 of the radio foot switch 6 monitors, by the detecting signal from the left-pedal detecting unit 11 or right-pedal detecting unit 12, whether left pedal 9 or right pedal 10 is pressed, as a main function of the radio foot switch 6.

For example, when the radio foot switch 6 sets the control operation of the ultrasonic operation apparatus 3, the left pedal 9 functions as the set pedal for outputting ultrasonic waves, and the right pedal 10 functions as the pedal for outputting the ultrasonic waves at the highest output level.

Meanwhile, when the radio foot switch 6 sets the control operation of the electric knife 5, the left pedal 9 is allocated to an incision mode and the right pedal 10 is allocated to the clot mode.

The information upon switching the pedal is displayed on a display unit 8a of the foot switch change-over device 8.

FIG. 3 shows the schematic structure of the ultrasonic operation apparatus 3.

The ultrasonic operation apparatus 3 comprises: an output unit 21 which outputs a (high-frequency) output signal for oscillating by the ultrasonic waves an ultrasonic generating unit (not shown) in the ultrasonic treatment tool 2; a CPU 22 which is connected to the output unit 21 and controls the output unit 21; a radio transmitting and receiving unit 23 which is connected to the CPU 22 and transmits and receives information by radio waves; a storing unit 24 which stores an operating program of the CPU 22 for controlling the operation of the ultrasonic operation apparatus 3 and stores the information including the ID code of the radio foot switch 6 for controlling by the radio waves the ultrasonic operation apparatus 3; and an ID code unit 25 which stores the ID code as the identification information specified to the ultrasonic operation apparatus 3.

When the radio foot switch 6 sets the control operation by radio waves of the ultrasonic operation apparatus 3, the left pedal 9 or right pedal 10 of the radio foot switch 6 is pressed, thereby transmitting an operating signal together with the ID code for designating the ultrasonic operation apparatus 3. Thus, the CPU 22 determines based on the ID code in the transmitted information whether or not the signal transmitted to the ultrasonic operation apparatus 3 is a signal for controlling the ultrasonic operation apparatus 3. Further, the radio CPU 22 controls the output unit 21 so as to perform the operation corresponding to the operating signal of the left pedal 9 or right pedal 10.

The internal structure of the electric knife 5 is not described because the schematic structure of the electric knife 5 is obtained by replacing the output unit 21 in FIG. 3 with a high-frequency output unit for outputting high-frequency current. Therefore the structure diagram of the electric knife 5 is omitted.

Referring to FIG. 4, the foot switch change-over device 8 comprises: a voice input unit 31 which receives a voice signal from the microphone 7; a CPU 32 which is connected to the voice input unit 31, decodes the processing of voice recognition of the voice signal inputted to the voice input unit 31 or the information transmitted from the radio foot switch 6 and displays the information on the display unit 8a; a radio transmitting and receiving unit 33 which is connected to the CPU 32 and transmits and receives information by radio waves; a storing unit 34 which stores an operating program of the CPU 32 that controls the operation of the foot switch change-over device 8 and stores the information including the ID code of the radio foot switch 6 for controlling by radio waves the foot switch change-over device 8; and an ID code unit 35 which stores the ID code as the identification information specified to the foot switch change-over device 8.

According to the first embodiment, the foot switch change-over device 8 receives the information transmitted by the radio waves from the radio foot switch 6 and displays the transmitted contents on the display unit 8a. Therefore, a user can know the medical device, serving as the set medical device as the control target, depending on the display contents of the display unit 8a.

Upon setting the medical device of the control target, necessary information can be confirmed.

Next, a description is given of the processing for setting a control switch of the medical device which controls the radio foot switch 6 as the feature of the present invention with reference to FIG. 5. According to the first embodiment, the foot switch change-over device 8 has a function for displaying information that is transmitted and received to/from the radio foot switch 6 and the medical device as the control target for transmitting and receiving the information to the radio foot switch 6.

Referring to FIG. 5, in step S1, the radio foot switch 6 is turned on and one of the left and right pedals is pressed. Thus, the medical device as the control target, e.g., the ultrasonic operation apparatus 3 is turned on (foot switch is abbreviated to an FS in FIG. 5 and the like for the purpose of a brief description).

In steps S2 to S4, the radio foot switch 6 is communicated with the turned-on medical device, thereby establishing such a communication control that the corresponding device executes the operation corresponding to the operation of the radio foot switch 6. The processing for establishing the communication control is as follows.

One of the left and right pedals is pressed in the radio foot switch 6 and a detecting signal indicating that the pedal is pressed is transmitted to the CPU 13. In step S2, as an initial operation (in which the ID code of the controllable medical device is not stored in the storing unit 15), the radio foot switch 6 transmits the ID code of the radio foot switch 6 as packet data together with a signal code indicating that the pedal is pressed.

The packet data includes the ID code of the radio foot switch 6 as the first source, the destination ID code for specifying the next-destination medical device, and a control code for the control operation (or operating code), e.g., a code of the operated pedal or a code corresponding to the operated pedal.

In the initialization, the medical device as the control target is not set to the storing unit 15 in the radio foot switch 6. Therefore, the portion of the ID code is blank or null, indicating that the destination ID code is not set.

In the ultrasonic operation apparatus 3, serving as the medical device as the control target, the CPU 22 initializes the control program of the ultrasonic operation apparatus 3, after that, receives the information transmitted from the radio foot switch 6, and recognizes based on the information that the received information is a signal for setting the medical device as the control target because the ID code of the medical device to be controlled is not set. Alternatively, the CPU 22 decodes based on the contents of the control code that the received information is a signal for setting the medical device as the control target.

In order to set the ultrasonic operation apparatus 3 to the medical device as the control target, in step S3, the ID code of the ultrasonic operation apparatus 3 is set to the source ID code and the ID code of the radio foot switch 6 is set as the destination code. Further, information on a setting code for the setting is transmitted as the control code.

In step S4, the radio foot switch 6 receives the medical device as the control target, that is, the information transmitted from the ultrasonic operation apparatus 3 in this case. The CPU 13 stores the ID code of the ultrasonic operation apparatus 3 to the storing unit 15 so as to set the ultrasonic operation apparatus 3 to the medical device as the control target.

The radio foot switch 6 comprises the two pedals 9 and 10. The radio foot switch 6 transmits, to the ultrasonic operation apparatus 3, inquiry information indicating which function of the ultrasonic operation apparatus 3 is allocated to the pedals 9 in accordance with the operation of the pedals 9 and 10. In response to an answer from the ultrasonic operation apparatus 3, the radio foot switch 6 allocates the function.

Further, the CPU 13 in the radio foot switch 6 transmits, to the ultrasonic operation apparatus 3, information on the reception completion of setting the ultrasonic operation apparatus 3, serving as the medical device as the control target.

The ultrasonic operation apparatus 3 receives the information indicating the reception completion and then the CPU 22 stores the ID code of the radio foot switch 6 in the storing unit 24.

The contents of transmitted and received information in this case are confirmed based on the information displayed on the display unit 8a of the foot switch change-over device 8.

After the above-mentioned communication establishment, in step S5, it is determined whether or not the pedal of the radio foot switch 6 is pressed (on-operation). The pedal code of the pressed pedal is transmitted together with the ID code for designating the medical device as the control target. Thus, in step S6, the medical device as the control target designated by the ID code, namely, the ultrasonic operation apparatus 3 reads the pedal code based on the received information and performs the corresponding operation. Then, the processing sequence returns to step S5.

For example, a function for outputting the setting is allocated to the left pedal 9 in the radio foot switch 6. A function for maximum output is allocated to the right pedal 10. The operator presses the left pedal 9 and, then, a set ultrasonic output is generated from the ultrasonic treatment tool 2. The operator presses the right pedal 10 and, then, the maximum ultrasonic output is generated from the ultrasonic treatment tool 2 so as to treat the organ.

In this case, the ID code indicating that the ultrasonic operation apparatus 3 is the control target is transmitted. Another medical device having another ID code does not erroneously operate by the ID in this case, when one of the remaining medical devices receives the operating code including the ID code from the radio foot switch 6 in response to the operation of the corresponding radio foot switch 6 and then the operating mode is excluded.

Meanwhile, when the pedal is not pressed, in step S7, the corresponding output stops and the processing sequence returns to step S5.

Finally, the ultrasonic operation apparatus 3 is turned off and then the information of the radio foot switch 6 is erased. The corresponding radio foot switch 6 can be used as a switch of another medical device.

In this case, when the ultrasonic operation apparatus 3 is turned off, the off-power of the ultrasonic operation apparatus 3 enables a reset signal fo r resetting the setting of the ultrasonic operation apparatus 3 to the medical device as the control target to be transmitted to the radio foot switch 6 together with the ID code of the ultrasonic operation apparatus 3. After receiving the return signal from the radio foot switch 6, the ultrasonic operation apparatus 3 may be turned off. In this case, the radio foot switch 6 erases the ID code of the ultrasonic operation apparatus 3 stored in the storing unit 15 upon setting the ultrasonic operation apparatus 3 to the medical device as the control target.

Therefore, another medical device can be set to the medical device as the control target again. For example, the electric knife 5 can be set to the medical device as the control target.

The series of operations shown in FIG. 5 are executed between the radio foot switch 6 and the electric knife 5. Thus, it is possible to obtain the same operations and advantages as those of the ultrasonic operation apparatus 3.

When the left pedal (incise pedal) 9 is pressed, an output for incision is generated from the electric knife treatment tool 4. When the right pedal (clot pedal) 10 is pressed, an output for clotting is generated from the electric knife treatment tool 4. Thus, the organ is treated.

According to the first embodiment, the medical device as the control target is not limited to the specific one. The medical device can arbitrarily be set to the medical device as the control target by the initialization and the like and can remotely be controlled by radio waves.

The user's operability is improved and the radio foot switch 6 is not limited to the specific medical device. Therefore, when one of the two dedicated medical devices is damaged, it is possible to prevent the inconvenience that the other is not used or must be repaired and the maintenance is improved.

According to another embodiment, in the initializing step after turning on the power, when the pedal of the radio foot switch 6 is pressed, it is recognized that the pressed switch is an output control switch of the turned-on medical device. In order to recognize that the pressed switch is the medical device after turning on the power, the power needs to be turned on again.

In order to solve the problem, a foot switch selecting button (not shown) may be arranged to the ultrasonic operation apparatus 3 or electric knife 5. The foot switch selecting button is pressed by pressing the pedal of the radio foot switch 6. Thus, the radio foot switch 6 may relate to the controlled medical device.

According to the embodiment, the medical device first to be controlled is turned on and the medical device is set to the medical device as the control target. After that, even when another medical device is turned on, the radio foot switch 6 remotely and certainly controls the medical device as the control target without erroneously operating the other medical device. Basically, when only the medical device as the control target is remotely controlled, the radio foot switch 6 may have transmitting means and the medical device as the control target may have receiving means.

In this case, by turning on only the medical device as the control target, only the medical device as the control target receives the transmitting signal of the radio foot switch 6, thus to execute the remote control operation without erroneous operation. In this case, when the medical device as the control target is turned off and thus the setting of the medical device as the control target is canceled. In addition, when another medical device as the control target is turned on, the other medical device is remotely controlled.

On the other hand, when another medical device is turned on, the radio foot switch 6 and the medical device as the control target have transmitting and receiving means. The transmitting and receiving means in the radio foot switch 6 and the medical device as the control target can transmit individual specific ID codes. The ID codes of the partner are stored (by the radio foot switch 6 and the medical device as the control target) and the source and destination are specified by the ID codes added to the transmitted signals. Then, the certain operation is ensured.

According to the first embodiment, the maintenance and the operability are improved in the radio foot switch and the medical device. The wiring of the operation room is reduced and the wiring space is further reduced.

According to the first embodiment, one medical device, one ultrasonic operation apparatus 3, or one electric knife 5 is set to the one radio foot switch 6. Preferably, the switching control needs the high operability and the switching control is easy.

That is, in the actual medical field, since a plurality of medical devices are controlled during the operation, the medical devices controlled by the radio foot switch 6 need to sequentially be switched and this will be described according to the second embodiment.

Second Embodiment

The structure according to the second embodiment of the present invention is basically the same as that according to the first embodiment. However, the foot switch change-over device has voice selecting means or the like which sets the medical device corresponding to one radio foot switch.

Hereinbelow, a description is given of the second embodiment with reference to FIGS. 4 and 6.

As described with reference to FIG. 4, the microphone 7 is connected to the foot switch change-over device 8, and the microphone 7 can read voice information of the user such as the operator.

Further, the storing unit 34 registers necessary voice data. The storing unit 34 receives the voice information, and when it is determined that the received voice information corresponds to the registered voice data as compared with the registered voice data, the control operation is performed corresponding to the voice data.

When the operator inputs "the ultrasonic operation apparatus" by voice and the voice is recognized as the ultrasonic operation apparatus, the foot switch change-over device 8 transmits, to the radio foot switch 6 and the ultrasonic operation apparatus 3, the information indicating the selection (of the ultrasonic operation apparatus 3 as the medical device as the control target).

In this case, as described according to the first embodiment, the radio foot switch 6 and the ultrasonic operation apparatus 3 are specified without fail by transmitting the signal additionally having the ID code for specifying the medical device as the destination.

Thereafter, the pedal of the radio foot switch 6 is pressed and then the electric knife 5 generates an output corresponding to the pedal. Then, the electric knife 5 keeps an output standby mode until the selection of the medical device, and performs the processing for preventing erroneous generation of outputs.

Similarly to the foregoing, when the "electric knife" is inputted or is recognized, the foot switch change-over device 8 transmits the signal indicating the selection to the radio foot switch 6 and the electric knife 5.

Then, the radio foot switch 6 is pressed and the electric knife treatment tool 4 generates an output of the corresponding pedal.

Meanwhile, until the ultrasonic operation apparatus 3 is selected again, the ultrasonic operation apparatus 3 keeps the output standby mode and performs the processing for preventing the erroneous generation of the output.

With the above-mentioned structure, the medical device is easily selected and switched and the one radio foot switch 6 can control the outputs of the each medical device.

Figure 6:
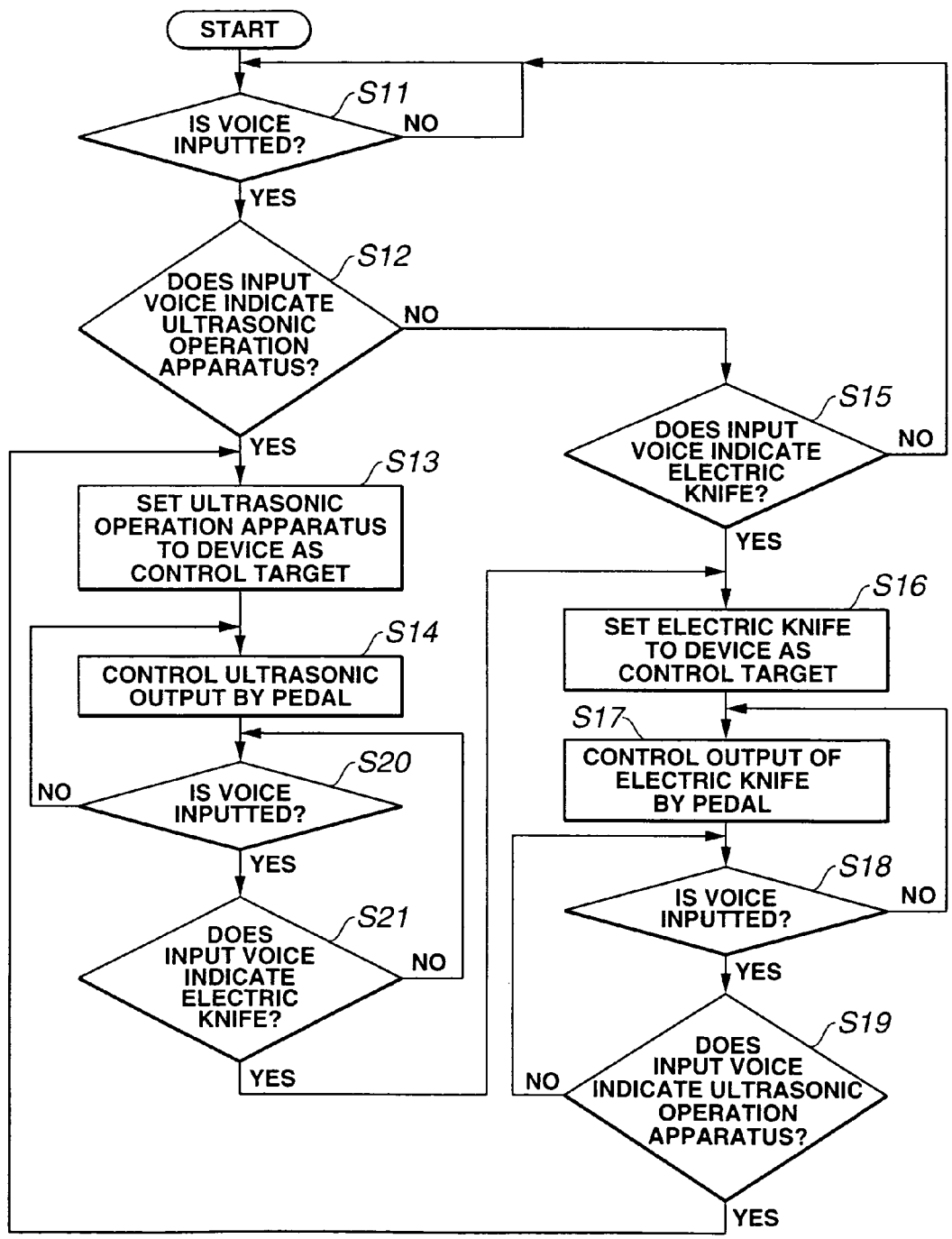
FIG. 6 is a flowchart showing the control operation according to a second embodiment of the present invention.

FIG. 6 is a flowchart showing the operation according to the second embodiment.

Referring to FIG. 6, the medical device is turned on and then, in step S11, the CPU 32 of the foot switch change-over device 8 determines whether or not the voice is inputted and waits for the voice input.

When the CPU 32 determines that the voice is inputted, in step S12, the CPU 32 determines based on the comparison with the registered data whether or not the voice input indicates the ultrasonic operation apparatus. When the CPU 32 determines that the voice input indicates the ultrasonic operation apparatus, in step S13, the CPU 32 of the foot switch change-over device 8 transmits information indicating the selection of the ultrasonic operation apparatus 3 as the medical device as the control target, additionally having the ID code, to the ultrasonic operation apparatus 3 and the radio foot switch 6.

The return signal indicating the reception of the information is received and CPU 32 transmits, to the radio foot switch 6 and the ultrasonic operation apparatus 3, a signal indicating the completion of selecting the ultrasonic operation apparatus 3 as the medical device as the control target, and the ultrasonic operation apparatus 3 is selected and is set to the medical device as the control target.

The display unit 8a displays the selection and setting of the ultrasonic operation apparatus 3 to the medical device as the control target. In step S14, the pedal of the radio foot switch 6 is operated and the ultrasonic operation apparatus 3 controls the ultrasonic output in accordance with the pedal.

On the other hand, in step S12, it is determined that the medical device as the control target is not the ultrasonic operation apparatus 3, the processing sequence shifts to step S15 whereupon it is determined based on the comparison with the registered data whether or not the medical device as the control target is the electric knife. If it is determined that the medical device as the control target is the electric knife, (through the same processing as that in step S13), in step S16, the electric knife 5 is selected and is set to the medical device as the control target.

The display unit 8a displays that the electric knife 5 is selected and is set to the medical device as the control target. In step S17, the pedal of the radio foot switch 6 is operated and thus the electric knife 5 controls an output of the electric knife in accordance with the pedal.

Then, in step S18, the foot switch change-over device 8 determines whether or not the voice is inputted. If the foot switch change-over device 8 determines that the voice is not inputted, the processing sequence returns to step S17. If the foot switch change-over device 8 determines that the voice is inputted, the processing sequence advances to step S19 whereupon it is determined whether or not the voice input indicates the ultrasonic operation apparatus.

If it is determined that the voice input indicates the ultrasonic operation apparatus, the processing sequence shifts to step S13 whereupon the ultrasonic operation apparatus 3 is selected and is set to the medical device as the control target. On the other hand, if it is determined that the voice input does not indicate the ultrasonic operation apparatus, the processing sequence returns to step S18.

As mentioned above, after setting the electric knife 5 to the medical device as the control target, the voice indicating the ultrasonic operation apparatus 3 is inputted, thereby changing the medical device as the control target from the electric knife 5 to the ultrasonic operation apparatus 3.

After step S14, in step S20, it is determined whether or not the voice is inputted. If determined that the voice is not inputted, the processing sequence returns to step S14. If it is determined that the voice is inputted, in step S21, it is determined whether or not the voice input indicates the electric knife 5. If it is determined that the voice input does not indicate the electric knife 5, the processing sequence returns to step S20. If it is determined that the voice input indicates the electric knife 5, the processing sequence shifts to step S16 whereupon the electric knife 5 is set to the medical device as the control target.

According to the second embodiment, the medical device as the control target can easily be changed by the voice and the operability is improved. Similarly to the first embodiment, advantageously, the maintenance is improved and the space is reduced.

According to the second embodiment, the voice is used as the switch input means of the foot switch. Further, the same operation and advantage are obtained by using a selecting switch.

Further, according to the second embodiment, the foot switch is used as the output control means. Further, a hand switch is used with the above-mentioned structure and thus the same operation and advantage are obtained.

In the foregoing, the operation is performed by using the one radio foot switch 6. When a plurality of operators simultaneously perform the operation, the destination ID code is added and then is transmitted. Thus, upon using a wireless remote control device such as the a plurality of radio foot switches 6, the remote control is independently performed between the plurality of remote control devices are the plurality of medical devices as the control targets.

Third Embodiment

Figure 7:
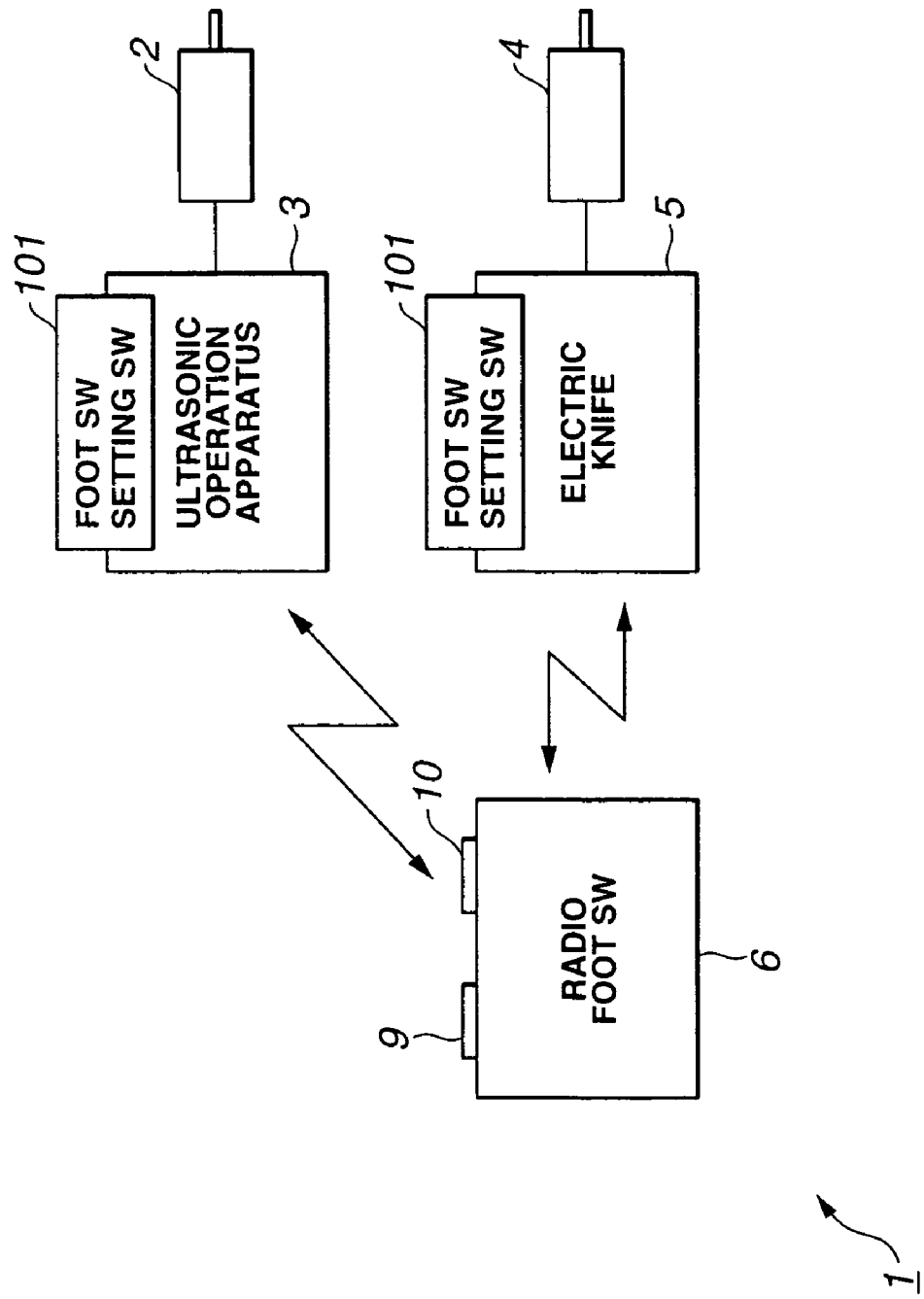
FIG. 7 is a diagram showing the entire structure of an electric operation system according to a third embodiment of the present invention.
Figure 8:
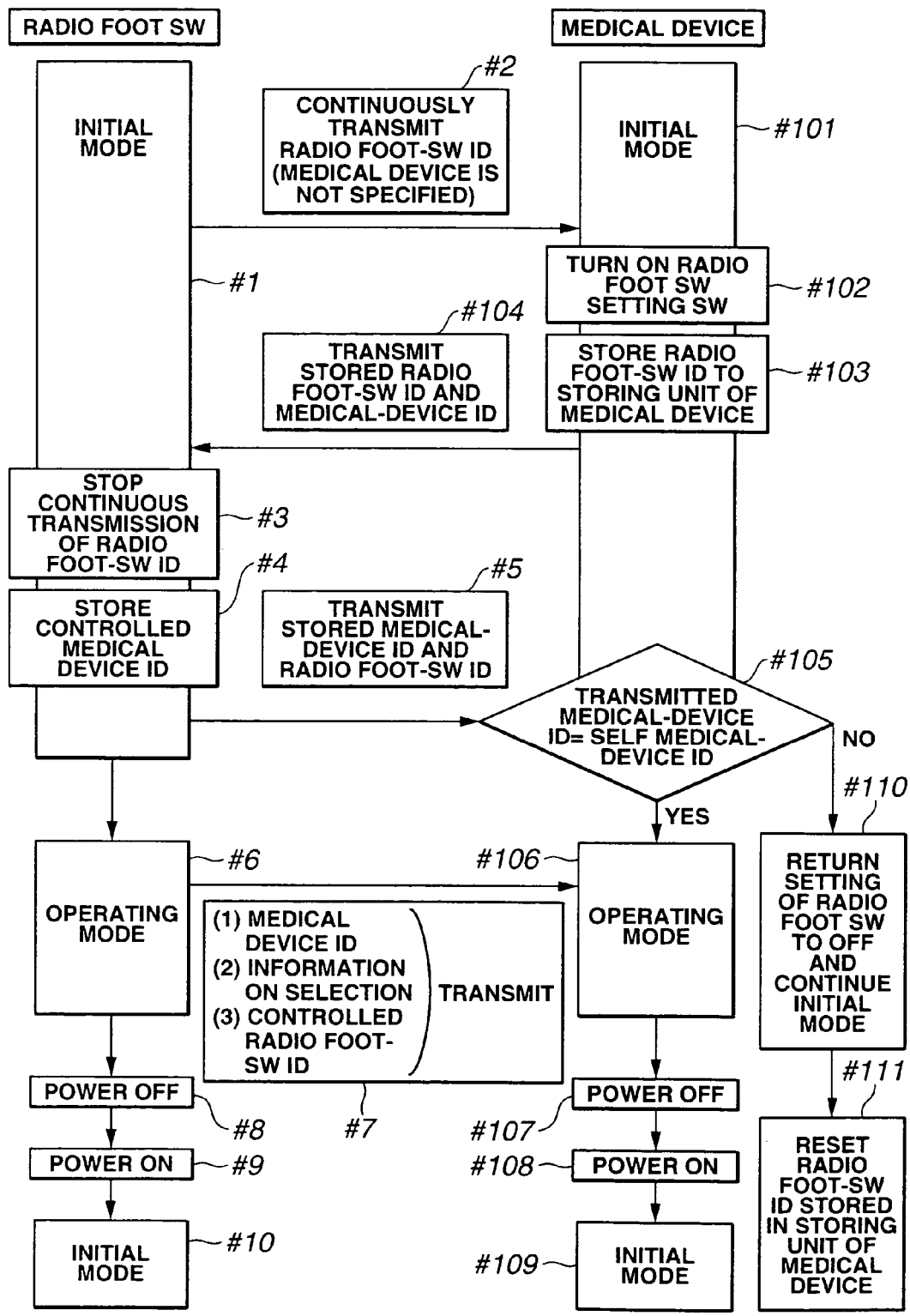
FIG. 8 is an explanatory diagram showing the operation of the electric operation system according to the third embodiment of the present invention.

FIG. 7 is a diagram showing the entire structure of an electric operation system according to a third embodiment of the present invention. FIG. 8 is an explanatory diagram showing the operation of the electric operation system according to the third embodiment of the present invention.

According to the third embodiment, unlike the electric operation system according to the first embodiment, only one foot switch is used and setting functions are concentrated in the medical device.

The radio foot switch 6 is turned on and then the corresponding foot switch shifts to an initial mode (#1) whereupon a self-recognizing code is continuously transmitted (#2).

Further, the medical device (e.g., ultrasonic operation apparatus 3) shifts to the initial mode after the turning-on operation (#101). In this case, the medical device which is controlled by the foot switch is not set and a plurality of turned-on medical devices can receive the ID code of the foot switch.

The medical device has its fixed medical device ID code, and receives, via the transmitting and receiving unit, a foot switch ID code that is continuously transmitted from the foot switch after the turning-on operation. The received foot switch ID code is stored in the storing unit (#103). The received foot switch ID code may be displayed on the medical device.

The medical device has a foot switch setting switch 101. The switch 101 is turned on (#102) and then the medical device sets and registers the control of the foot switch setting switch 101. The medical device transmits the medical device ID code and the foot switch ID code stored in the storing unit to the radio foot switch in a mode for initializing the medical device (#104).

When the received foot switch ID code matches the foot switch ID code, the radio foot switch stores the similarly received medical device ID code into the storing unit (#4). After that, the radio foot switch transmits, to the medical device, the foot switch ID code and the medical device ID code stored in the storing unit (#5). Then, the radio foot switch shifts to an operating mode (#6).

As long as the operating mode does not end, even if the radio foot switch receives another medical device ID code, the corresponding medical device ID code is refused, and the controlled medical device ID is not replaced. The radio foot switch continuously transmits its radio foot switch ID in the initial mode. However, after shifting to the operating mode, the radio foot switch stops the continuous transmission of the radio foot switch ID (#3).

When the received medical device ID code matches the self medical device ID code and the received radio foot switch ID code matches the radio foot switch ID code stored in the storing unit (#105), the medical device thereafter shifts to the operating mode (#106).

When the received radio foot switch does not match the radio foot switch ID code stored in the storing unit in step #105, the initial mode continues (#110) and the radio foot switch ID stored in the storing unit of the medical device is reset (#111).

As long as the operating mode does not end, even if the medical device receives another foot switch ID code, the ID code of the foot switch ID code is refused. The controlled foot switch ID is not replaced.

Only when both the radio foot switch and the medical device are in the operating mode, the pedal of the radio foot switch is pressed and then the corresponding medical device (e.g., ultrasonic operation apparatus) operates. In this case, when the radio foot switch has a plurality of pedals, the output control corresponding to the pedals is managed by the specific pedal ID.

When the pedal is pressed, the specific pedal ID indicating which pedal of the radio foot switch is pressed is transmitted to the medical device as the control target together with the medical device ID as the control target and the radio foot switch ID (#7). The medical device which receives the information operates in accordance with the pedal ID.

The medical device in the operating mode is turned off (#107) and then the operating mode ends. Sequentially, the medical device is turned on (#108) and then the initial mode starts (#109). Then, the ID code of the self radio foot switch is continuously received.

Similarly, the power of the radio foot switch in the operating mode is turned off (#8) and then the operating mode ends. Sequentially, the power of the radio foot switch is turned on (#9) and then the initial mode starts (#10) and then the ID code of the self radio foot switch is continuously transmitted.

Fourth Embodiment

Figure 9:
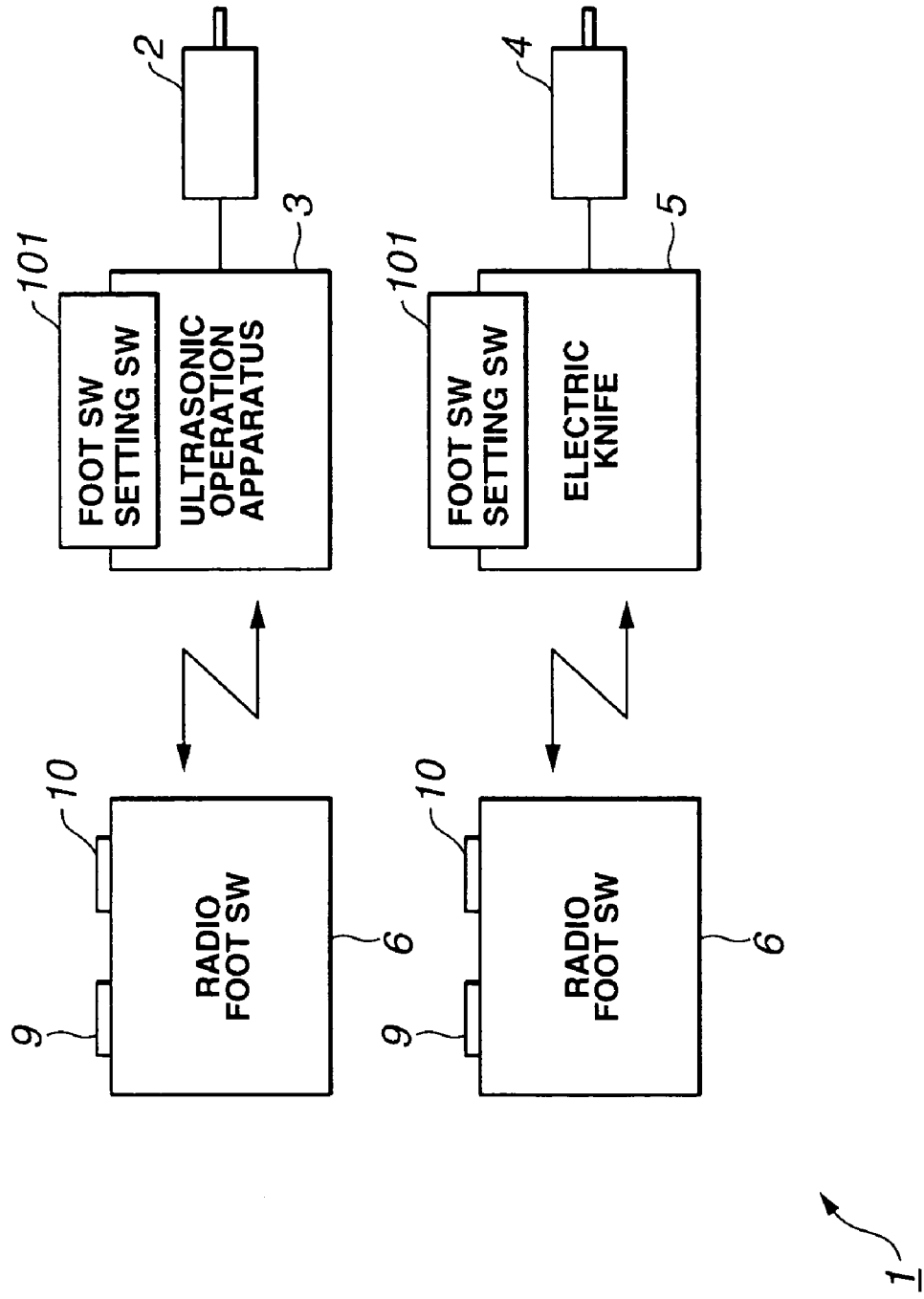
FIG. 9 is a diagram showing the entire structure of an electric operation system according to a fourth embodiment of the present invention.
Figure 10:
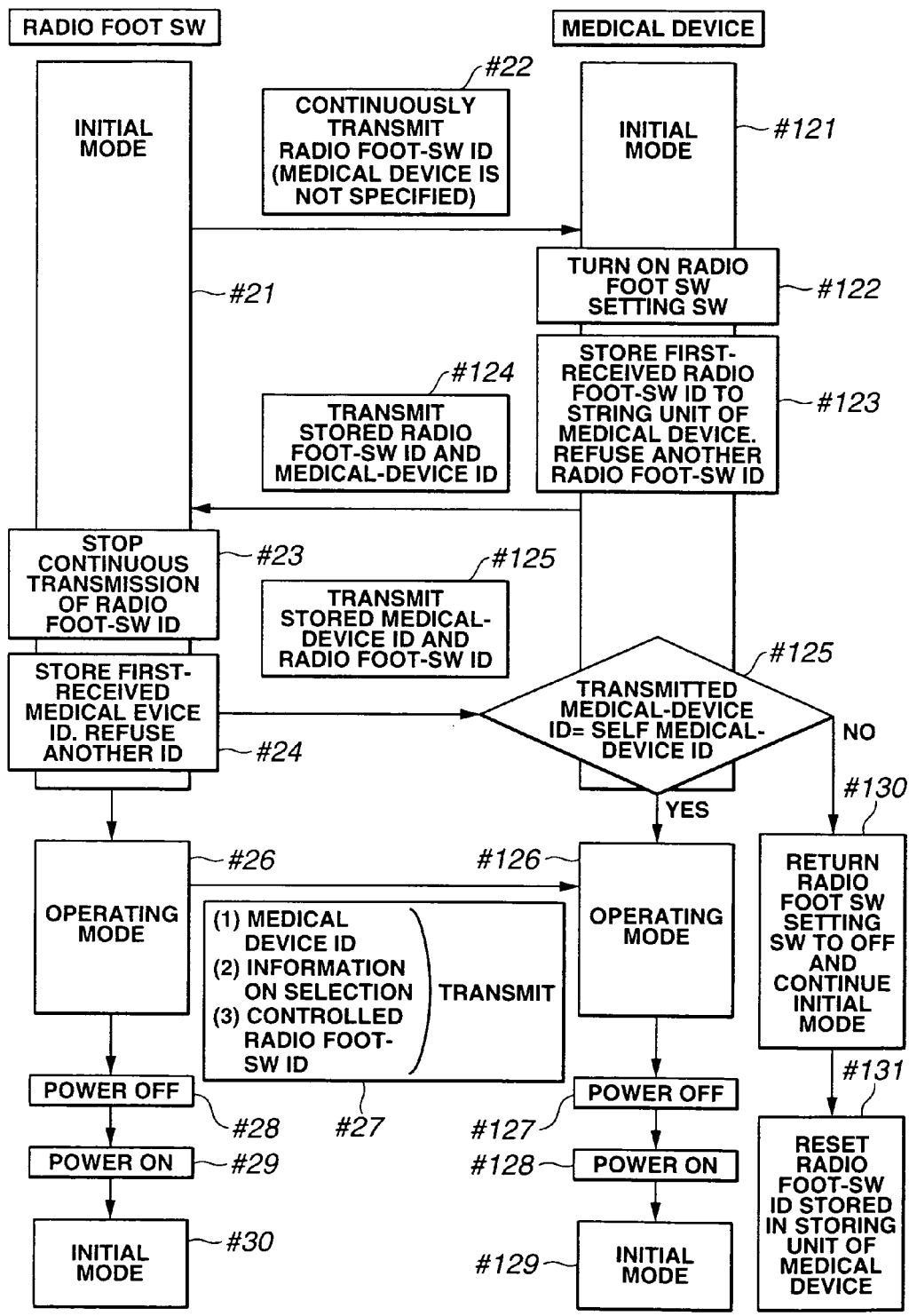
FIG. 10 is an explanatory diagram showing the operation of the electric operation system according to the fourth embodiment of the present invention.
Figure 11:
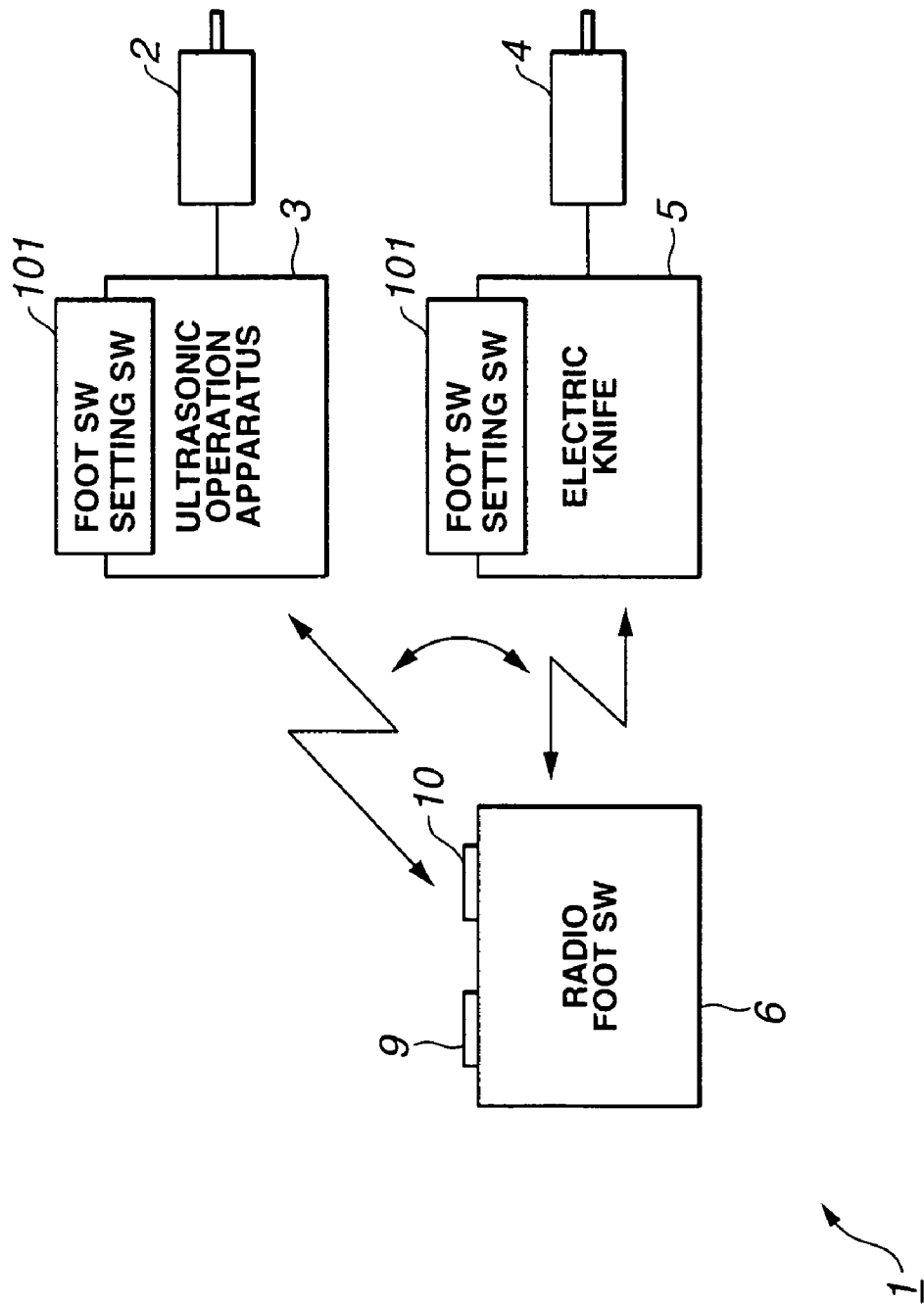
FIG. 11 is a diagram showing the entire structure of an electric operation system according to a modification of the fourth embodiment of the present invention.

FIG. 9 is a diagram showing the entire structure of an electric operation system according to a fourth embodiment of the present invention. FIG. 10 is an explanatory diagram showing the operation of the electric operation system according to the fourth embodiment of the present invention. FIG. 11 is a diagram showing the entire structure of an electric operation system according to a modification of the fourth embodiment of the present invention.

The setting functions are concentrated on the medical device according to third embodiment. Unlike the third embodiment, according to the fourth embodiment, when a plurality of radio foot switches are provided in the operation room and a plurality of foot switches to be used are provided, the foot switches are individually allocated to the medical devices. According to the modification of the fourth embodiment, when a plurality of foot switches to be used in the system are provided, the number of the radio foot switches to be used may be limited to one.

According to the fourth embodiment, first, one medical device in the system is turned on and then a plurality of foot switches enter the initial mode (#21), and the radio foot switch ID is continuously transmitted (#22). When the plurality of radio foot switches use a base band system that does not multiplex the signal, the plurality of radio switch IDs compete against each other. The plurality of competing radio foot switches are ordered under the access control such as CSMA/CD (Carrier Sense Multiple Access/Collision Detection). The CSMA/CD (Carrier Sense Multiple Access/Collision Detection) detects the carrier, checks if the carrier is used, and when the carrier is not used, the signal is transmitted. The radio foot switches check the carriers and, when the timing is the same, the transmission collides with each other (collision). Then, the signal is monitored during the transmission and, when the collision is detected, the reset operation is performed (random time is waited and the signal is re-transmitted).

Under the access control such as the CSMA/CD., the plurality of radio foot switches continuously transmit the self radio foot switch IDs. The medical devices store the radio foot switch ID into the storing unit (#123). Alternatively, the medical devices may display the radio foot switch ID.

The medical devices have the foot switch setting switch 101. The foot switch setting switch 101 is turned on (#122), the medical device sets and registers that it is controlled by the foot switch setting switch 101, the medical device ID code and the foot switch ID code stored in the storing unit are transmitted to the radio foot switch in the mode for initializing the medical device (#124).

When the received foot switch ID code matches the foot switch ID code of the self radio foot switch, the radio foot switch stores the received medical device ID code into the storing unit (#24). After that, the radio foot switch transmits the foot switch ID code and the medical device ID code stored in the storing unit to the medical device (#25). Then, the radio foot switch shifts to the operating mode (#26).

When the ID codes do not match in step #125, the initial mode continues (#120). The radio foot switch setting switch is turned off, and the ID of the radio foot switch stored in the storing unit of the medical device is rest (#121).

While the operating mode does not end, even if the radio foot switch receives the ID code of another medical code, the ID code of the medical device is refused, and the controlled medical device ID is not replaced. In the initial mode, the radio foot switch continuously transmits the self radio foot switch ID. However, after the initial mode shifts to the operating mode, the continuous transmission of the self radio foot switch ID is stopped (#23).

When the received medical ID code matches the self medical device ID code and the received radio foot switch ID code matches the radio foot switch ID code stored in the storing unit (#125), the medical device shifts to the operating mode (#126). While the operating mode does not end, even if another radio foot switch ID code is received, the foot switch ID code is refused, and the controlled foot switch ID is not replaced.

The radio foot switch for controlling the medical device might be simultaneously stored in another medical device. Among the plurality of medical devices which store the same radio foot switch ID, the priority is given to the medical device which early stores, in the radio foot switch, the transmission of the radio foot switch ID and the self medical device ID to the foot switch. After that, the radio foot switch transmits, to the medical device, the radio foot switch ID code and the medical device ID code stored in the storing unit. Then, the radio foot switch shifts to the operating mode. On the other hand, the medical device which stores the IDs afterwards repeats the re-transmission during a predetermined time and does not receive the transmission of the radio foot switch ID code and the self medical device ID code from the radio foot switch. Thus, the time is out and the medical device returns to the original initial mode and enters a receiving mode of another radio foot switch.

When the number of the radio foot switches to be used in the operation system is limited to one (refer to FIG. 11), the time-out medical devices store the radio foot switch ID code. The medical device may be controlled so that another radio foot switch ID code is not received.

Only when the radio foot switch and the medical device are in the operating mode, the corresponding medical device (e.g., ultrasonic operation apparatus) operates by pressing the pedal of the radio foot switch. When the radio foot switch has a plurality of pedals, the output control corresponding to the pedal is managed by the specific pedal ID. Upon pressing the pedal, the specific pedal ID indicating which pedal is pressed by the radio foot switch is transmitted to the medical device as the control target together with the medical device ID as the control target and the radio foot switch ID (#27). The medical device which receives the information performs output in accordance with the pedal ID.

The medical device in the operating mode is turned off (#127) and thus the operating mode ends. Sequentially, when the medical device is turned on (#128) and then the initial mode starts (#129) and the ID code of the self radio foot switch can continuously be received.

The radio foot switch in the operating mode is similarly turned off (#28) and thus the operating mode ends. Sequentially, the corresponding radio foot switch is turned on (#29), the initial mode starts (#30) and the self radio foot switch ID can continuously be transmitted.

Fifth Embodiment

Figure 12:
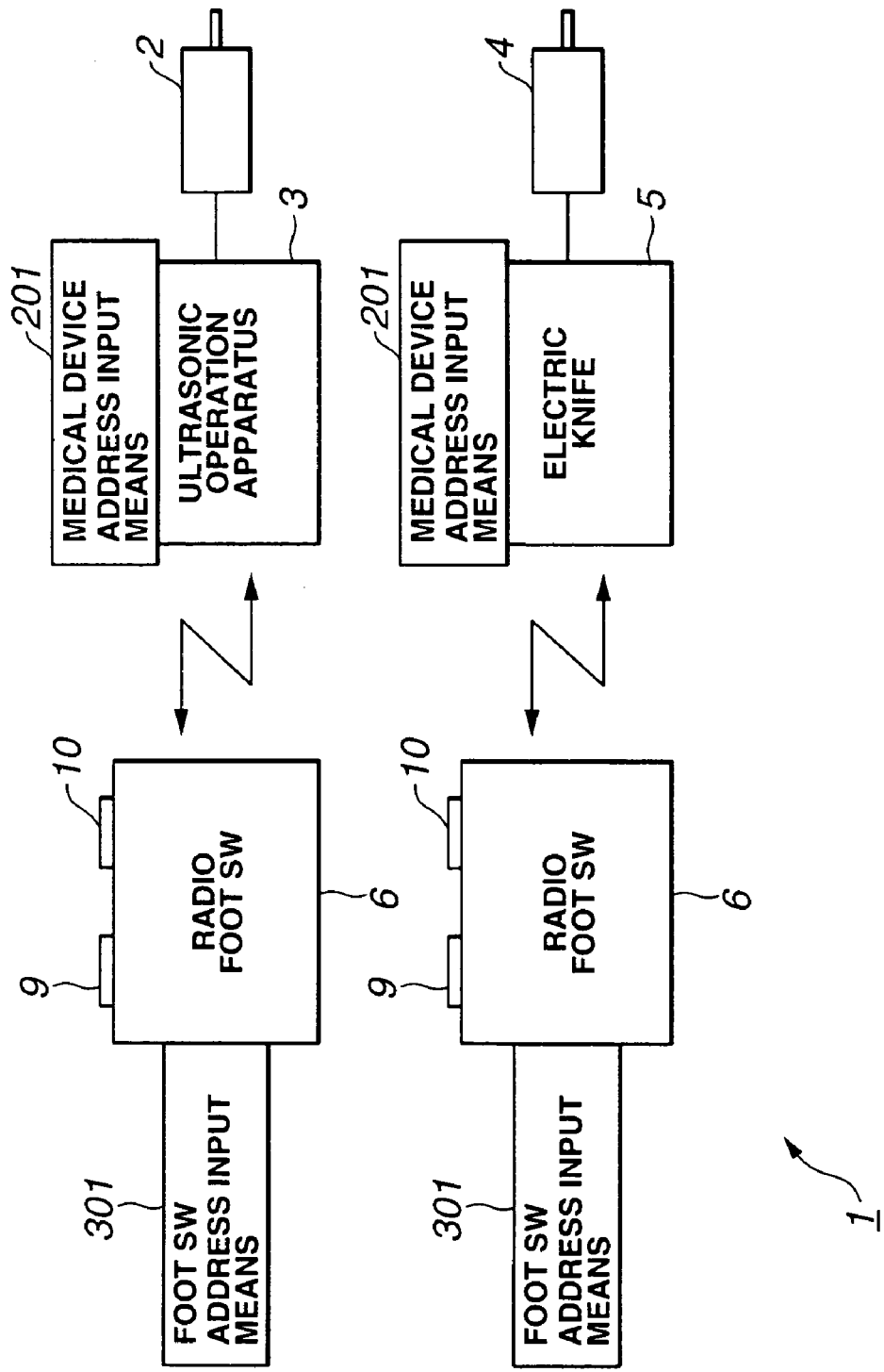
FIG. 12 is a diagram showing the entire structure of an electric operation system according to a fifth embodiment of the present invention.
Figure 13:
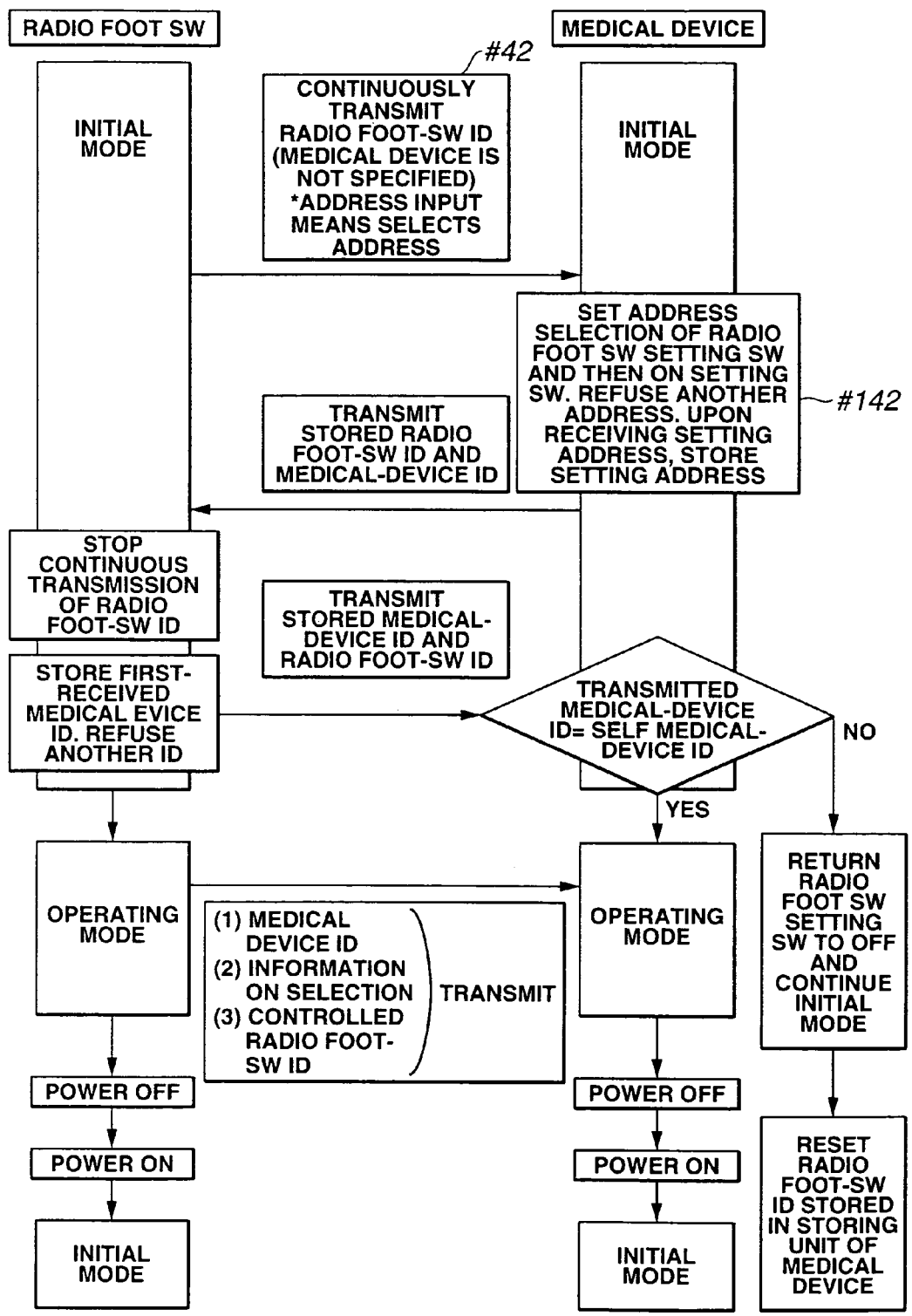
FIG. 13 is an explanatory diagram showing the operation of the electric operation system according to the fifth embodiment of the present invention.

FIG. 12 is a diagram showing the entire structure of an electric operation system according to the fifth embodiment of the present invention. FIG. 13 is an explanatory diagram showing the operation of the electric operation system according to the fifth embodiment of the present invention.

According to the fifth embodiment, the plurality of radio foot switches and medical devices individually comprise address input means (foot switch address input means 301 and medical device address input means 201) and thus a predetermined radio foot switch among the plurality of radio foot switches has a one-to-one relationship with a predetermined medical device. Although not shown, similarly to the third embodiment, the medical devices have the foot switch setting switches according to the fifth embodiment of the present invention.

According to the fifth embodiment, in step #2 according to the third embodiment, an address is designated and the ID code is transmitted (#42). On the other hand, the medical device sets the foot switch setting switch to the address and then the setting switch is turned on. Other addresses are refused and, when the corresponding setting address is received, the received address is stored (#142).

Other operations are the same as those according to the third embodiment.

According to the fifth embodiment, the radio foot switch and the medical device have an ID setting function with a predetermined range. Therefore, the operation system is able to comprise the plurality of radio foot switches and medical devices without increasing the digit number of the radio foot switch ID and the medical device ID. Further, the ID setting function of the radio foot switches and the medical devices are shared within a predetermined range. The radio foot switch and the medical device are easily exchanged or system is easily changed. A communication interface may be GP-IB or the like.

Sixth Embodiment

Figure 14:
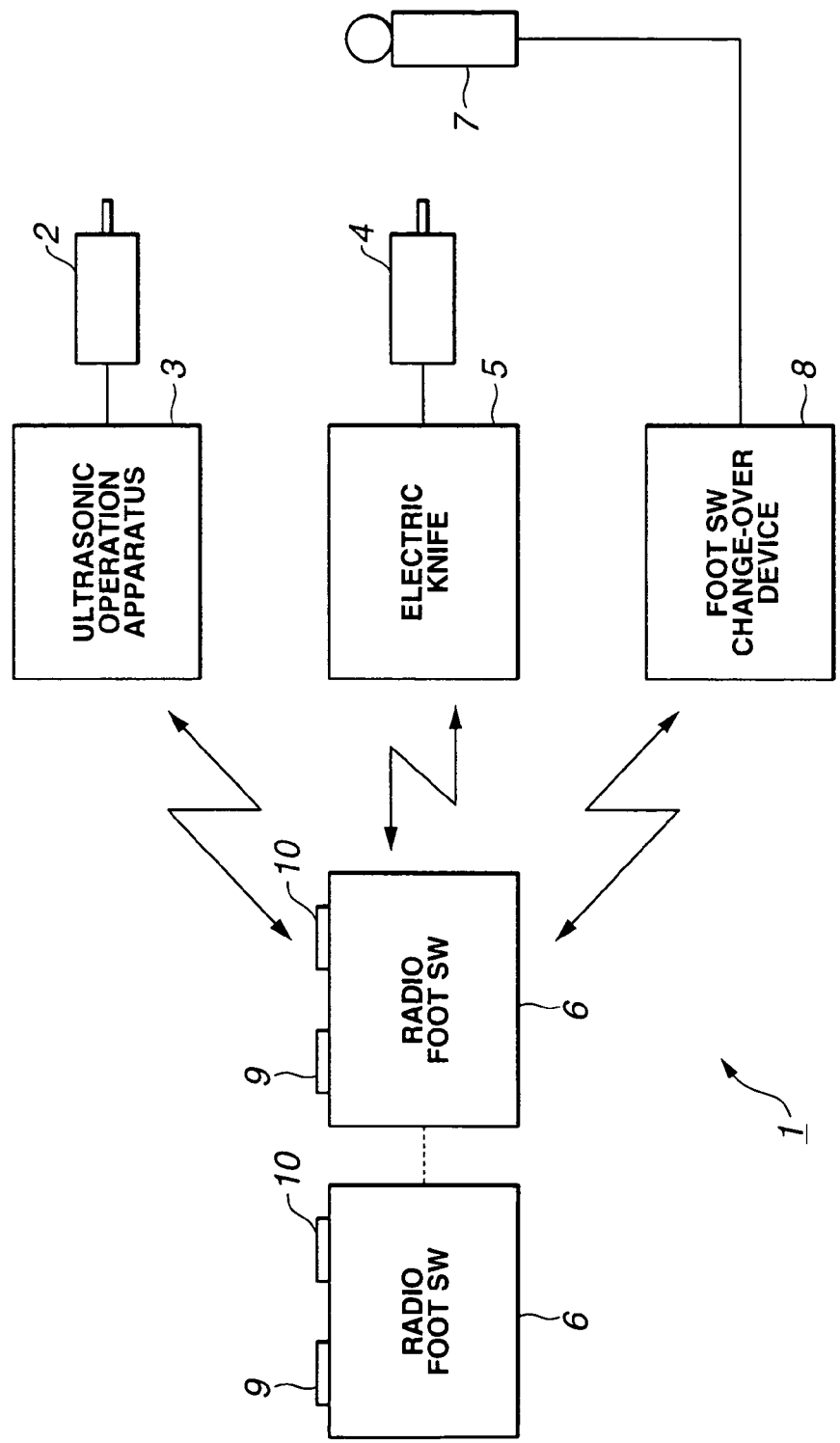
FIG. 14 is a diagram showing the entire structure of an electric operation system according to a sixth embodiment of the present invention.
Figure 15:
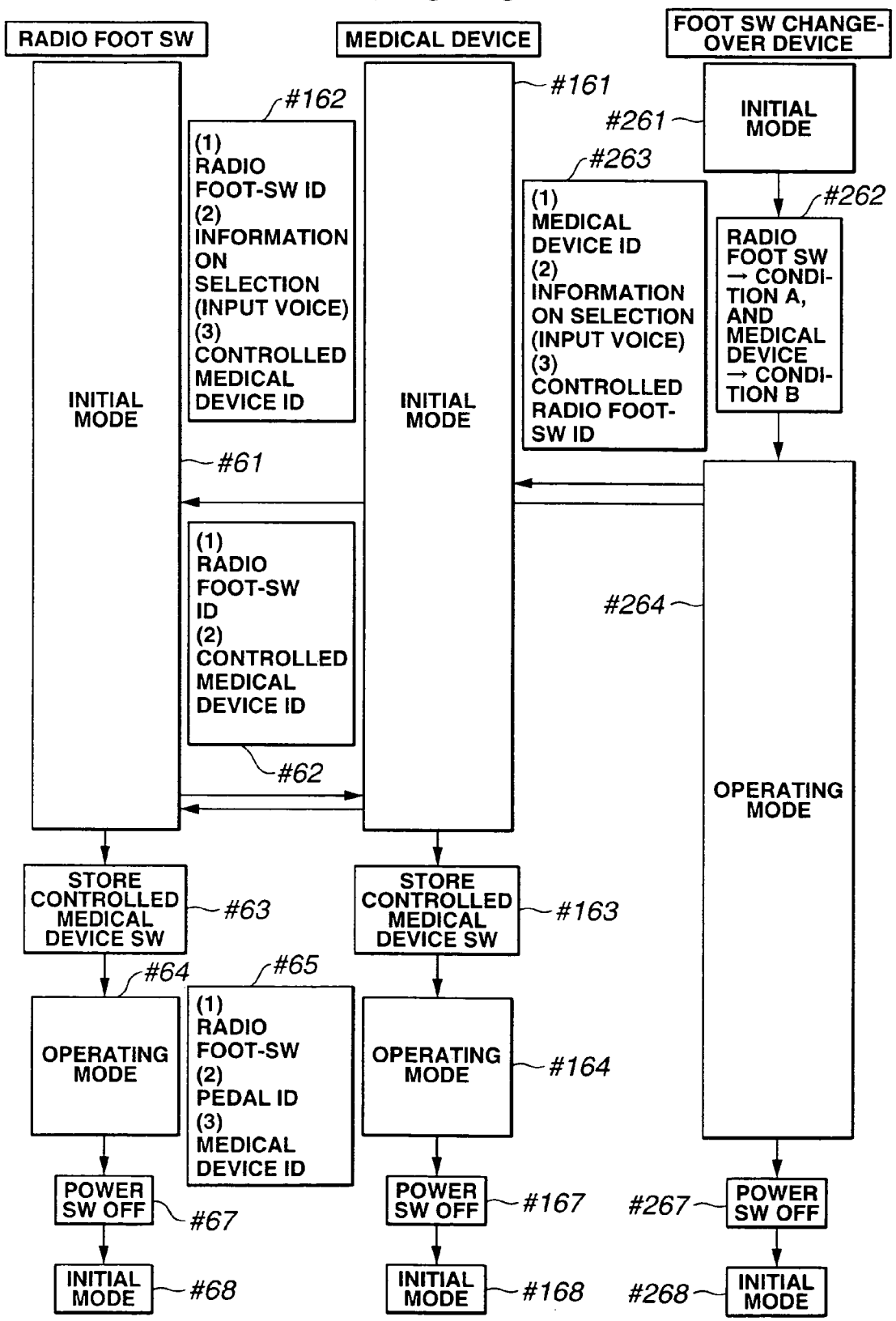
FIG. 15 is an explanatory diagram showing the operation of the electric operation system according to the sixth embodiment of the present invention.

FIG. 14 is a block diagram showing the schematic diagram of an electric operation system according to the sixth embodiment of the present invention. FIG. 15 is an explanatory diagram showing the operation of the electric operation system according to the sixth embodiment of the present invention.

The sixth embodiment is basically the same as the second embodiment (refer to FIG. 1). However, a plurality of radio foot switches are provided, and are replaced and are used. A predetermined radio foot switch is allowed to have a corresponding relationship with the medical device. When the radio foot switch and the medical device shift to the operation mode, the control signal is transmitted and received only between the radio foot switch and the medical device.

The medical device and the radio foot switch are turned on and shift to the initial mode (#61 and #161). In the initial mode, the medical device or the radio foot switch continuously transmits its medical device ID to the foot change-over device.

The foot switch change-over device is turned on and shifts to the initial mode (#261). The foot switch change-over device comprises a medical device ID storing unit which can store the IDs of a predetermined N medical devices and storing unit which can store the IDs of a predetermined M radio foot switches. In this case, a plurality of radio foot switches use the base band system which does not multiplex signals and then the plurality of radio foot switches compete against each other. As mentioned above, the access using the same base band is controlled under the access control such as CSMA/CD (Carrier Sense Multiple Access/Collision Detection). When the electric operation system comprises more than the predetermined N medical devices or more than the predetermined M medical devices, more than a predetermined number of IDs are repeatedly re-transmitted within a predetermined time and the time is out.

The foot switch change-over device has N or less IDs stored in the storing unit for the radio foot switch or M or less IDs stored in the storing unit for the medical device. Further, when the newly-received ID does not exist within a predetermined time or when N is the number of IDs stored in the storing unit for the radio foot switch which has been stored in the storing unit or M is the number of IDs stored in the storing unit for the medical device, the foot switch change-over device shifts to the operating mode (#264).

After the mode shifts to the operating mode, the foot switch change-over device 8 selects the medical device as the control target or the radio foot switch to be controlled, by recognizing the voice through an external microphone or change-over switch. The radio foot switch transmits, to the selected medical device, the corresponding medical device ID or the radio foot switch ID corresponding to the selected radio foot switch.

The pedal of the radio foot switch is pressed, thereby transmitting, to the foot switch change-over device, the radio foot switch ID, pedal ID, and driving command of the radio foot switch. The foot switch change-over device which receives the information transmits, to the corresponding medical device, the medical ID of the selected medical device together with the driving command and the pedal ID. The transmitted medical device performs corresponding output control.

Under the control operation, the medical device and the radio foot switch recognize the information on the selected medical device and radio foot switch, and the radio foot switch directly transmits, to the corresponding medical device, the control signals including the radio foot switch ID, pedal ID, and the medical device ID.

Alternatively, such a system can be structured that the medical device ID and the radio foot switch ID are transmitted and stored between the selected medical device and the radio foot switch and thus the medical device ID and the driving command are driving-controlled between the directly-selected radio foot switch and the selected medical device, not via the foot switch change-over device.

According to the sixth embodiment, upon exchanging the radio foot switch or one medical device, the foot switch change-over device is turned off and further the medical device is turned off.

The off-power resets the storage in the storing unit of the foot switch change-over device, the medical device, and the radio foot switch. Sequentially, the foot switch change-over device is turned on and, then, the foot switch change-over device starts from the initial mode, thus receiving and setting in the previous manner the medical device ID code of the medical device that is continuously transmitted and the radio foot switch ID code.

Seventh Embodiment)

Figure 16:
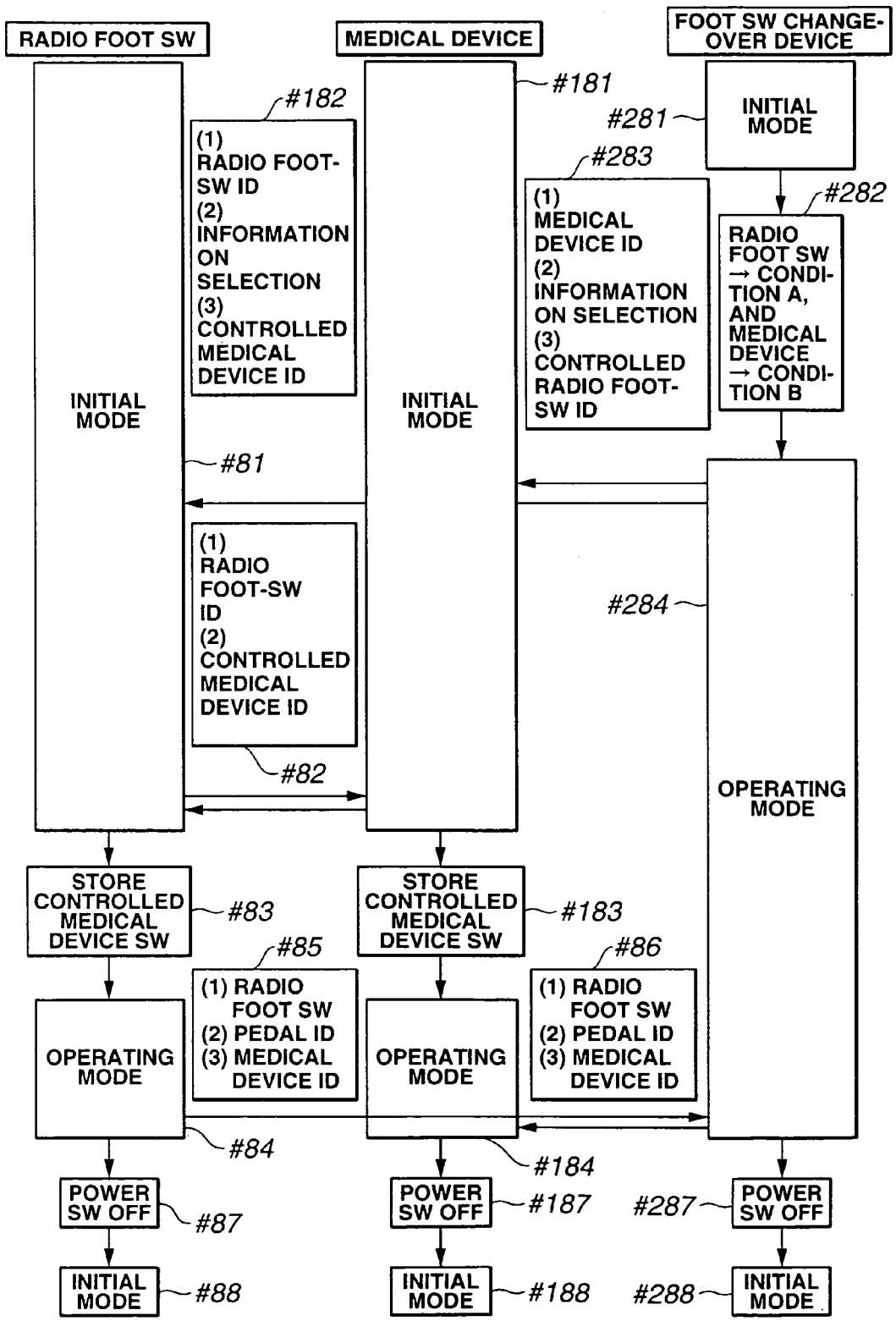
FIG. 16 is a diagram showing the operation of an electric operation system according to a seventh embodiment of the present invention.

FIG. 16 is an explanatory diagram showing the operation of an electric operation system according to the seventh embodiment of the present invention.

The seventh embodiment has the same structure as that according to the sixth embodiment. Unlike the sixth embodiment, in the electric operation system according to the seventh embodiment which switches, by the foot switch change-over device, the medical device that operates, the medical device or radio foot switch is registered in the foot switch change-over device upon starting the electric operation system, and the output control (on/off operation) of the radio foot switch is performed via the foot switch change-over device.

According to the seventh embodiment, in the structure according to the sixth embodiment, the exchange of the medical device or radio foot switch to be used is assumed in the foot switch change-over device, thus to change the system.

According to the sixth embodiment, in order to exchange the medical device or radio foot switch which constitutes the system, at least foot switch change-over device needs to recognize the ID of the new medical device or foot switch change-over device after exchanging the medical device or radio foot switch which constitutes the system. According to the seventh embodiment, the system and the structure will be obvious.

According to the seventh embodiment, the medical device, the radio foot switch, and the foot switch change-over device are turned on. The turning-on order of the devices may be arbitrary, and any device may first be turned on.

The medical device and the radio foot switch are turned on and then shift to the initial mode. In the initial mode, the medical device or radio foot switch continuously transmits its medical device ID to the foot switch change-over device. The foot switch change-over device is turned on and then shifts to the initial mode. The foot switch change-over device comprises: a medical device ID storing unit which stores IDs of a predetermined N pieces of medial devices; and a storing unit which stores IDs of a predetermined M pieces of medical device. In this case, when a plurality of radio foot switches use the base band system which does not multiplex the signal, the plurality of radio foot switch IDs compete against each other. However, the access using the same base band is controlled under the access control such as CSMA/CD (Carrier Sense Multiple Access/Collision Detection). When the electric operation system comprises more than the predetermined N medical devices or more than the predetermined M medical devices, more than a predetermined number of IDs are repeatedly re-transmitted within a predetermined time and the time is out.

The foot switch change-over device has N or less IDs stored in the storing unit for the radio foot switch or M or less IDs stored in the storing unit for the medical device. Further, when the newly-received ID does not exist within a predetermined time or when N is the number of IDs stored in the storing unit for the radio foot switch which has been stored in the storing unit or M is the number of IDs stored in the storing unit for the medical device, the foot switch change-over device shifts to the operating mode.

After the mode shifts to the operating mode, the foot switch change-over device selects the medical device as the control target or the radio foot switch to be controlled, by recognizing the voice through an external microphone or change-over switch. The radio foot switch transmits, to the selected medical device, the corresponding medical device ID or the radio foot switch ID corresponding to the selected radio foot switch.

The pedal of the radio foot switch is pressed, thereby transmitting, to the foot switch change-over device, the radio foot switch ID, pedal ID, and driving command of the radio foot switch. The foot switch change-over device which receives the information transmits, to the corresponding medical device, the medical ID of the selected medical device together with the driving command and the pedal ID. The transmitted medical device performs corresponding output control. Under the control operation, the foot switch change-over device concentratedly manages and controls the information on the selected medical device and the radio foot switch. In order to have a corresponding relationship between the selected medical device and radio foot switch, on/off information of the radio foot switch is transmitted to the foot switch and the pedal ID and the driving command are transmitted to the corresponding medical device based on the corresponding information stored in the foot switch.

Alternatively, such a system is structured that the medical device ID and the radio foot switch ID are transmitted and stored between the selected medical device and the radio foot switch and thus the medical device ID and the driving command are driving-controlled between the directly-selected radio foot switch and the selected medical device, not via the foot switch change-over device.

According to the seventh embodiment, upon exchanging the radio foot switch or one medical device, the foot switch change-over device is turned off and further the medical device is turned off. The off-power resets the storage in the storing unit of the foot switch change-over device, the medical device, and the radio foot switch. Sequentially, the foot switch change-over device is turned on and, then, the foot switch change-over device starts from the initial mode, thus receiving and setting in the previous manner the medical device ID code of the medical device that is continuously transmitted and the radio foot switch ID code.

The present invention is not limited to the above embodiments and can variously be modified without departing from the essentials of the present invention.

INDUSTRIAL APPLICABILITY

According to the present invention, a plurality of medical devices are easily controlled.

CROSS-REFERENCE OF RELATED APPLICATION

The present application is based on the priority of Japanese Patent Application No. 2002-290411 filed to Japan on Oct. 2, 2002. The disclosure is referred to the description, claims, and drawings of the present invention.

The invention claimed is:

1. An operation system having a plurality of medical devices and a remote control device for remotely controlling the medical devices, each of the medical devices having an identification code, the remote control device having an identification code, the remote control device comprising:

a remote control side transmitting and receiving unit which can communicate with the medical devices;

a remote control side storing unit which stores or outputs identification codes of the medical devices, which are received from the medical devices via the remote control side transmitting and receiving unit;

a remote control side output circuit which outputs the identification code of the remote control device;

remote control side control means which determines a target medical device from the plurality of medical devices based on an instruction from a user of the operation system, transmits the identification code of the target medical device, the identification code of the remote control device, and a driving control command to the target medical device via the remote control side transmitting and receiving unit;

and a radio foot switch, operable to transmit the identification code of the remote control device to the target medical device and operate the target medical device, including at least one pedal which is operable to control the operation of the target medical device, each of said plurality of medical devices comprising:

a medical device side transmitting and receiving unit which can communicate with the remote control device;

a medical device side storing unit which stores or outputs the identification code of the remote control device, which is received from the remote control device via the medical device side transmitting and receiving unit;

a medical device side output circuit which outputs the identification code of the medical device;

medical device side control means which drives the medical device, when the identification code of the remote control device in association with the driving command, which is received via the medical device side transmitting and receiving unit, matches the identification code of the remote control device, which is stored in the medical device side storing unit and when the identification code of the target medical device in association with the driving command and determined by the remote control device, which is received via the medical device side transmitting and receiving unit, matches the identification code of the medical device, which is outputted from the medical device side output circuit.

2. The operation system according to claim 1, wherein at least one of the identification code of the medical device, which is stored in the remote control side storing unit and is received from the medical device via the remote control side transmitting and receiving unit, and the identification code of the remote control device, which is stored in the medical device side storing unit and is received from the remote control device via the medical device side transmitting and receiving unit, can be replaced with a new medical device identification code or a new remote control device identification code.

3. The operation system according to claim 1, wherein:

the medical device stores or outputs the identification code of the remote control device, which is received from the medical device via the medical device side transmitting and receiving unit of the medical device, after turning on the medical device, and the medical device transmits, via the medical device side transmitting and receiving unit to the remote control device, the identification code of the remote control device and the identification code of the medical device.

4. The operation system according to claim 1, further comprising:

a medical device changeover device, wherein the medical device change-over device transmits the selected information to the medical device which is remotely controlled by the remote control device.

5. The operation system according to claim 4, further comprising:

a medical device switching device which can select a medical device to be selected by voice.

6. The operation system according to claim 4, further comprising:

a medical device switching device which can select a medical device to be selected by a switch.

7. The operation system according to claim 1, wherein the pedal is operable by pressing.

8. An operation system having a plurality of medical devices and a remote control device for remotely controlling the medical devices, each of the medical devices having an identification code, the remote control device having an identification code, the remote control device comprising:

remote control side transmitting and receiving means which can communicate with the medical device;

remote control side storing means which stores or outputs identification codes of the medical devices, which are received from the medical devices via the remote control side transmitting and receiving means;

remote control side output means which outputs the identification code of the remote control device;

remote control side means which determines a target medical device from the plurality of medical devices based on an instruction from a user of the operation system, transmits the identification code of the target medical device, the identification code of the remote control device, and a driving control command to the target medical device via the remote control side transmitting and receiving means; and a radio foot switch, operable to transmit the identification code of the remote control device to the target medical device and operate the target medical device, including at least one pedal which is operable to control the operation of the target medical device, each of said plurality of medical devices comprising:

medical device side transmitting and receiving means which can communicate with the remote control device;

medical device side storing means which stores or outputs the identification code of the remote control device, which is received from the remote control device via the medical device side transmitting and receiving means;

medical device side output means which outputs the identification code of the medical device;

medical device side means which drives the medical device, when the identification code of the remote control device in association with the driving command, which is received via the medical device side transmitting and receiving means, matches the identification code of the remote control device, which is stored in the medical device side storing means, and when the identification code of the target medical device in association with the driving command and determined by the remote control device, which is received via the medical device side transmitting and receiving means, matches the identification code of the medical device, which is outputted from the medical device side output means.

9. The operation system according to claim 8, wherein the pedal is operable by pressing.

* * * * *

UNITED STATES PATENT AND TRADEMARK OFFICE
CERTIFICATE OF CORRECTION

PATENT NO.        : 7,563,259 B2
APPLICATION NO. : 10/958868
DATED             : July 21, 2009
INVENTOR(S)       : Hiroyuki Takahashi It is certified that error appears in the above-identified patent and that said Letters Patent is hereby corrected as shown below:

On the Title Page, Item (30) should read,

(30) Foreign Application Priority Data

October 2, 2002 (JP) .................2002-290411

Signed and Sealed this

Twentieth Day of October, 2009

David J. Kappos
*Director of the United States Patent and Trademark Office*